US006399377B1

United States Patent
Mory

(12) United States Patent
(10) Patent No.: US 6,399,377 B1
(45) Date of Patent: *Jun. 4, 2002

(54) USE OF ANTI-SENSE SEQUENCES TO INCREASE RESPONSIVENESS TO GENE AMPLIFICATION

(76) Inventor: Yves Mory, 15 Moskovitz Street, 76474 Rehovot (IL)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/077,253
(22) PCT Filed: Nov. 27, 1995
(86) PCT No.: PCT/US95/15098
§ 371 (c)(1), (2), (4) Date: Feb. 3, 1999
(87) PCT Pub. No.: WO97/20055
PCT Pub. Date: Jun. 5, 1997

(51) Int. Cl.$^7$ .............................. C12N 5/10; C12N 15/85
(52) U.S. Cl. .................... 435/375; 435/320.1; 435/325; 536/23.1
(58) Field of Search .................. 435/6, 69.1, 91.1, 435/455, 325, 375, 320.1, 91.4; 536/23.1, 24.3, 24.5

(56) References Cited

U.S. PATENT DOCUMENTS 4,399,216 A 8/1983 Axel et al.
4,912,040 A 3/1990 Kaufman et al.

FOREIGN PATENT DOCUMENTS

WO    WO 88/03558    5/1988

OTHER PUBLICATIONS

Gu et al., Cytotechnology 9(1–3) P. 237–45, 1992.*
Branch, TIBS 23, pp. 45–50, Feb./1998.*
Anderson, Nature vol. 392/Supp, pp. 25–30, Apr./1998.*
Izant, et al., Inhibition of Thymidine Kinase Gene Expression by Anti–Sense RNA: A Molecular Approach to Genetic Analysis, Cell, vol. 36, pp. 1007–1015, Apr. 1984.
Kaufman, et al., Amplification and Expression of Sequences Cotransfected with a Modular Dihydrofolate Reductase Complementary DNA Gene, J. Mol. Biol., vol. 159, pp. 601–621, 1982.
Kaufman, Randal J., Selection and Coamplification of Heterologous Genes in Mammalian Cells, Methods in Enzymology, vol. 185, pp. 537–566, 1990.
Lacatena, et al., Base pairing of RNA I with its complementary sequence in the primer precursor inhibits ColE1 replication, Nature, vol. 294, pp. 623–626, Dec. 17, 1981.

(List continued on next page.)

*Primary Examiner*—John L. LeGuyader
*Assistant Examiner*—M Schmidt
(74) *Attorney, Agent, or Firm*—Iver P. Cooper

(57) ABSTRACT

A method for regulating the production level of a desired protein in a transformed mammalian cell, comprising: a directly amplifiable gene sequence, in expressable form, which when expressed renders said cell more resistant to a toxic agent; a gene of interest, in expressible form, which encodes a desired protein foreign to said cell; and an anti-sense gene sequence, in transcribable form, encoding an anti-sense RNA capable of selectively hybridizing to at least a portion of the mRNA transcribed from said directly amplifiable gene sequence so as to inhibit the translation of said mRNA, such that a higher level of amplification of said directly amplifiable gene and said gene of interest can be achieved, if the cell is exposed to a sufficient level of the toxic agent, that in the absence of said anti-sense RNA.

13 Claims, 12 Drawing Sheets

OTHER PUBLICATIONS

Maher III, et al., Comparative hybrid arrest by tandem antisense oligodeoxyribonucleotides or oligodeoxyribonucleoside methylphosphonates in a cell–free system, Nucleic Acids Research, vol. 16, No. 8, pp. 3341–3358, 1988.

Mizuno, et al., A unique mechanism regulating gene expression: Translational inhibition by a complementary RNA transcript (micRNA), Proc. Natl. Acad. Sci. USA, vol. 81, pp. 1966–1970, Apr. 1984.

Ringold, et al., Co–Expression and Amplification of Dihydrofolate Reductase cDNA and the *Escherichia coli* XGPRT Gene in Chinese Hamster Ovary Cells, Journal of Molecular and Applied Genetics, vol. 1, pp. 165–175, 1981.

Sartorius, et al., Hybridization arrest of the cell–free translation of the malarial dihydrofolate reductase/thymidylate synthase mRNA by anti–sense oligodeoxyribonucleotides, Nucleic Acids Research, vol. 19, No. 7, pp. 1613–1618, 1991.

Tomizawa, et al., Inhibition of ColE1 RNA primer formation by a plasmid–specified small RNA, Proc. Natl. Acad. Sci. USA, vol. 78, No. 3, pp. 1421–1425, Mar. 1981.

Li, Li–Jing et al., "Establishment of a chinese hamster ovary cell line that expresses grp78 antisense transcripts and suppresses A23187 induction of both GRP78 and GRP94.", Journal of Cellular Physiology, vol. 153. No. 3, pp. 575–582 (1992).

McIvor, R. et al., "Isolation and characterization of a variant dihydrofolate reductase cDNA from methotrexate–resistant murine L5178Y cells.", Nucleic Acids Research, vol. 18, No. 23, pp. 7025–7032 (1990).

Shotkoski, Frank et al., "Expression of an antisense dihydrofolate reductase transcript in transfected mosquito cells: effects on growth and plating efficiency.", Am. J. Trop. Med. Hyg., vol. 50, No. 4, pp. 433–439 (1994).

Wang, Sijian et al., "Quantitative evaluation of intracellular sense: antisense RNA hybrid duplexes.", Nucleic Acids Research, vol. 18, No. 18, pp. 4383–4391 (1993).

* cited by examiner

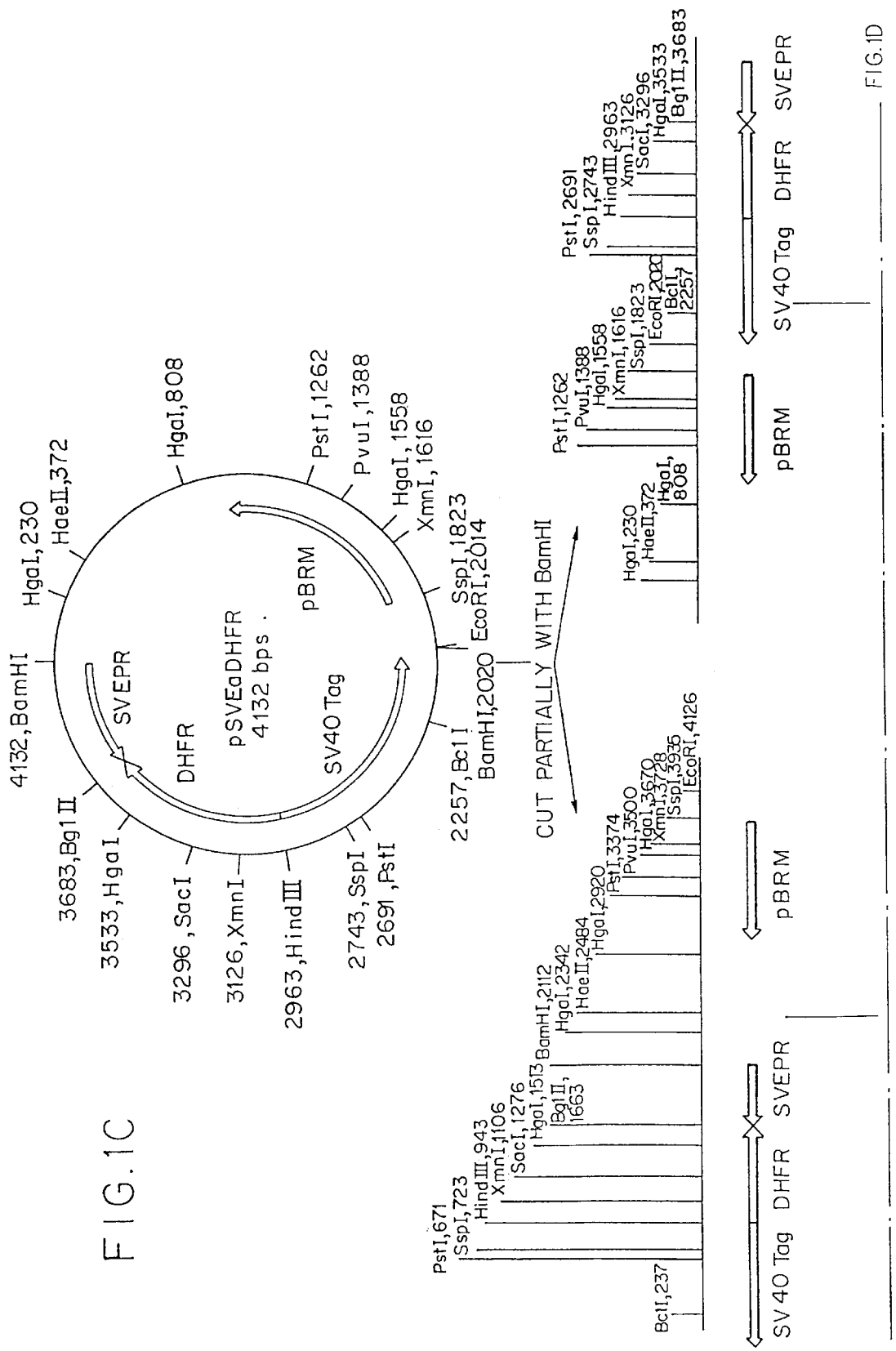

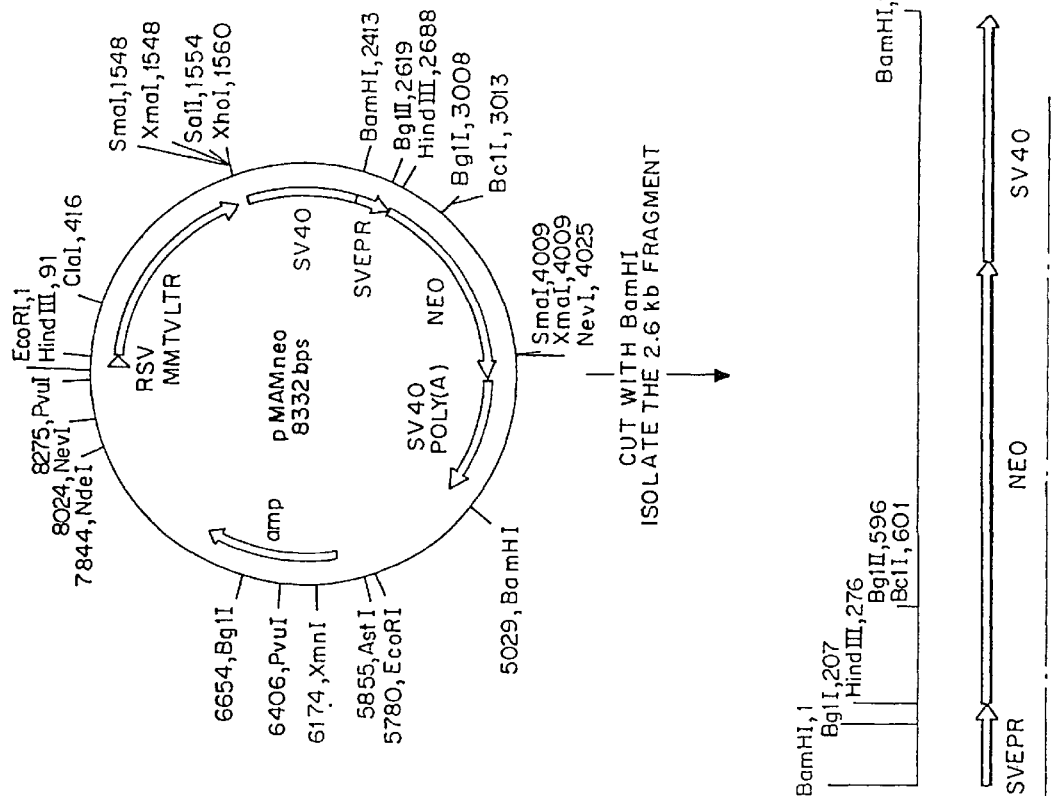
FIG.1E
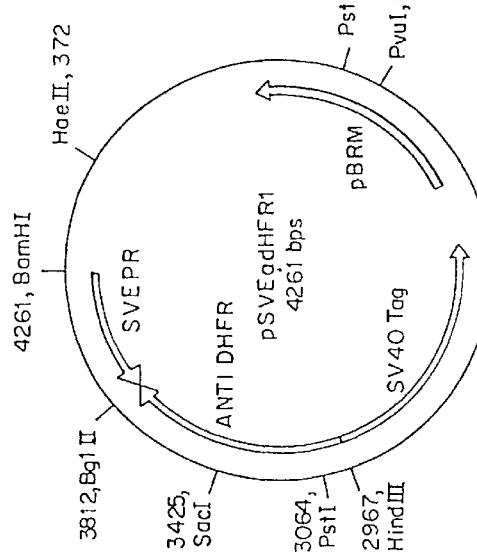
FIG.1F
FIG.1G

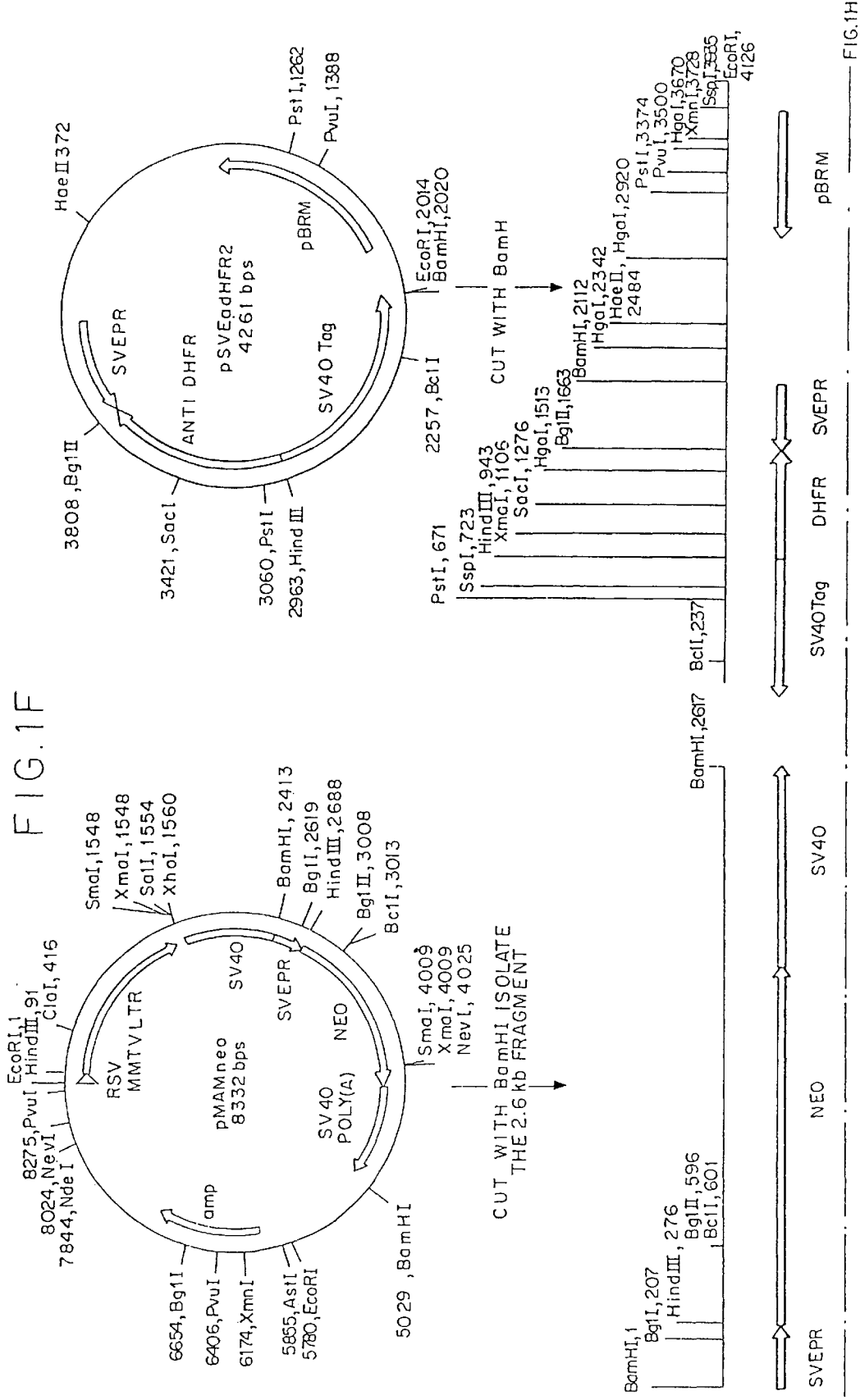

USE OF ANTI-SENSE SEQUENCES TO INCREASE RESPONSIVENESS TO GENE AMPLIFICATION

This application is a 371 of PCT/US95/15098, filed Nov. 27, 1995.

BACKGROUND OF THE INVENTION

1. Field of the Invention

The present invention is generally in the field of mammalian gene expression systems used for the cell culture production of proteins.

In particular, the present invention concerns new gene expression systems for increasing the efficiency and the amount of protein production in eukaryotic cell lines and, in particular, the well-known chinese hamster ovary (CHO) cell culture systems which utilize the dihydrofolate reductase (DHFR)—methotrexate (MTX) gene expression amplification system for the production of a wide variety of medically and veterinarily important proteins on a commercial scale. These new expression systems which employ new gene-expression enhancing vectors containing an anti-sense DHFR gene sequence, permit higher levels of protein production in eukaryotic cells at significantly lower levels of MTX, i.e. these eukaryotic cells are rendered more MTX-sensitive.

2. Description of the Background Art

DHFR/TX Mediated Gene Amplification

Many medically and veterinarily important proteins are produced using the CHO cell culture system in which gene expression is amplified by the DHFR/MTX system (Kaufman, R. J., Methods in Enzymol. 185, 537–566 (1990)). This system was developed in the early 1980's (see Axel, U.S. Pat. No. 4,399,216; Ringold et al., J. Mol. Appl. Genet. 1:165–175 (1981); Kaufman et al., J. Mol. Biol. 15:601–621 (1982)). Examples of proteins produced by this system are interleukins, interferons, receptors, human factor IX, human factor VIII, bovine luteinizing hormone, and others.

In the known CHO DHFR/MTX protein production systems, the CHO cell lines are usually DHFR$^-$ and as such, they can only grow in the essential absence of methotrexate. These CHO cell lines are then transformed or co-transformed with a plasmid/vector carrying a gene sequence encoding the protein of choice to be expressed together with the DHFR gene carried either on the same vector or on a different one. When expressed, the enzyme DHFR serves as a selectable marker for these transformed cells. The vector is usually of the type which can undergo stable recombination and hence subsequent stable incorporation into the genome of CHO DHFR$^-$ cells thereby rendering such cells DHFR$^+$ in a stable and constitutive manner.

The positively transformed DHFR$^+$ cells are selected by growing the cells in a standard culture medium, in which DHFR$^-$ cells cannot grow, and subjecting the cell cultures to a number of culture cycles or passages. Such a medium usually contains sufficient methotrexate to kill DHFR cells but which is generally not lethal to the DHFR$^+$ cells. This gives rise to stably transformed DHFR$^+$ cells, i.e., in which the entire transforming vector or co-transforming vectors or the essential portions thereof such as the DHFR$^+$ sequence and sequences adjacent thereto which include the gene encoding the protein of choice are stably integrated into the host chromosome. These stably transformed DHFR$^+$ cells are further cultured and cloned, i.e., individual colonies of cells are taken and cultured separately to provide a number of cloned, transformed DHFR$^+$ cell lines. These DHFR$^+$ cell lines are then examined for their ability to express the desired protein and those cell lines showing good expression (i.e., expressing the protein of choice in its expected form either as an intact protein or as an intact fusion product, depending on how the gene encoding the protein of choice was originally constructed on the transforming vector) are selected.

Axel et al., U.S. Pat. No. 4,399,216, discloses a system for co-transforming eukaryotic cells with a foreign DNA encoding a desired proteinaceous material and with an unlinked DNA encoding a selectable phenotype such as DHFR conferring methotrexate resistance. Alternatively, Axel et al. discloses amplifying a gene encoding a desired protein linked to the DNA encoding a selectable phenotype by challenging with successively higher amounts of the selecting agent.

The addition of MTX during cell culture causes gene amplification of gene sequences at and around the DHFR sequence, such as large stretches of flanking DNA that include the gene sequence encoding the desired protein (when unlinked DNAs are cotransfected into a cell, they tend to form a cointegrate that link the DNAs prior to integration into the host genome by non-homologous recombination). This results in an increased number of copies of these sequences and consequently, also results in elevated levels of both DHFR and the desired protein. The degree of amplification is regulated by the MTX inhibitory effect of DHFR.

However, the above CHO DHFR/MTX system has a number of drawbacks, the major one being that the necessary constitutive expression of the DHFR gene during cell culture results in increased levels of DHFR which act to inhibit the effect of MTX. Thus, as the cell culture progresses through successive stages of amplifying stable transfectants from the previous stage, more and more MTX is required for gene amplification until a limit is reached whereby the elevated MTX levels become toxic to the cells; in other words, the upper concentration limit of MTX to which the cells are still MTX-resistant is reached. Accordingly, the current CHO protein production systems have an upper limit as to the amount of desired protein that can be produced. The level of constitutive heterologous (desired) protein expression is relatively limited; for example, only production levels of as high as 10–30 mg/l of culture can be obtained after MTX treatment. Consequently, in order to further increase the amounts of protein produced in these systems, either additional cultures are required or larger cultures need to be grown, which adds considerably to the production costs. As mentioned above, current CHO protein production systems are employed for the production of medically and veterinarily important proteins on a commercial scale. There has therefore been a long-felt need to improve these systems to increase the amount of desired protein produced, on the one hand, and on the other hand, to reduce the costs for producing this increased amount of protein.

Anti-Sense DNA

Anti-sense RNA is transcribed from an upstream promoter of a coding sequence oriented in the anti-sense direction, i.e., opposite the normal or sense direction of the DNA and its transcribed sense RNA. The expression of anti-sense RNA complementary to the sense RNA is a powerful way of regulating the biological function of RNA molecules. Through the formation of a stable duplex between the sense RNA and anti-sense RNA, the normal or sense RNA transcript can be rendered inactive and untranslatable.

In prokaryotes, anti-sense RNA is believed to control plasmid COLE1 replication (Tomizawa et al., Proc. Nat'l. Acad. Sci. USA 78:1421, 1981; Lacatena et al., Nature 294:623,1981) and regulation of outer membrane protein production (Mizuno et al., Proc. Nat'l Acad. Sci. USA 81:1966,1984) as well as many others. Izant et al., Cell 36:1007 (1984), showed that anti-sense RNA also inhibits gene expression in eukaryotes. They constructed a plasmid with a promoter directing the transcription of an anti-sense RNA complementary to the normal thymidine kinase (tk) transcript which substantially reduced expression of the normal thymidine kinase gene.

Besides the thymidine kinase gene and the outer membrane protein genes OmpF and OmpC, anti-sense DNA sequences have been used to express anti-sense RNA complementary to normal or sense RNA transcripts of numerous genes. As an example, Kaufman et al., U.S. Pat. No. 4,912,040, discloses a system for expressing an anti-sense GRP78 DNA sequence capable of hybridizing to part or all of the endogenous GRP78 (similar to immunoglobulin heavy chain binding protein)—encoding mRNA transcript and thereby preventing its translation into GRP78 protein.

Anti-sense DNA to DHFR or DHFR-TS complex has also been reported. Wang et al., Nucl. Acids Res. 21:4383–4391 (1993) transfected expression vectors carrying anti-sense DHFR cDNAs into a DHFR over-expressing KB (epidermoid carcinoma) cell line to quantitatively evaluate stoichiometric effects on RNA hybrid duplex formation.

Sartorius et al., Nucl. Acids Res. 19:1613 (1991) showed inhibition of the in vitro translation of *Plasmodium falciparum* mRNA coding for the endogenous bifunctional enzyme dihydrofolate reductase-thymidylate synthase (DHFR-TS) with oligodeoxynucleotides directed against the translation initiation site or a site in the TS-coding region. Maher et al., Nucl. Acids Res. 16:3341–3358 (1988) also used anti-sense oligonucleotides to test arrest of in vitro translation of human DHFR mRNA. However, Maher's oligonucleotides contained either anionic diester or neutral methyl phosphonate internucleoside linkages prepared by automated synthesis.

Shotkoski et al., J. Trop. Med. Hyg. 50:433–439 (1994) expressed the mosquito DHFR gene, in both the sense and anti-sense orientations, under the control of a temperature-inducible promoter, in mosquito cells. Expression of the DHFR sense gene had little effect on cell growth, while expression of the anti-sense DHFR compromised cell growth and viability. Clones transfected with the sense construct retained significantly higher copy numbers of foreign DNA than did those receiving the anti-sense vector.

However, anti-sense DHFR has not previously been used to increase the responsiveness of DHFR$^+$ cells to methotrexate.

SUMMARY OF THE INVENTION

The present invention is based on the surprising and unexpected discovery that upon transfection of a eukaryotic cell line that is DHFR$^+$, MTX-resistant and capable of producing a desired protein, with a vector encoding an anti-sense DHFR sequence, the cell line became more responsive (sensitive) to MTX, thus allowing higher production levels of gene amplification and hence higher production levels of the desired protein at lower MTX levels. Even higher levels of protein production can be achieved by increasing MTX levels to the upper limit where the cells are still MTX-resistant. In some cases, the increased level of protein production was 500% (5-fold) higher than that achieved for control cultures not transformed with anti-sense DHFR-encoding plasmid.

It is therefore an object of the present invention to provide an anti-sense DHFR sequence, which may be introduced into eukaryotic MTX-resistant cells and upon expression of the anti-sense DHFR sequence, lead to a reduction in the amount of DHFR produced in the cells and hence a reduction in the amount of MTX required for gene amplification, with the result that increased amounts of protein can be produced at lower MTX levels (i.e. the cells are rendered more MTX-sensitive).

The present invention also provides an expression enhancing system for regulating the amount of protein production in eukaryotic cells having protein production levels regulated by a DHFR/MTX regulatory system. The expression enhancing system comprises an expression enhancing vector according to the present invention, that is capable of transfecting eukaryotic cells which are DHFR$^+$ and MTX-resistant, and which produce, under suitable conditions, a desired protein product and, when expressed in the eukaryotic cell line, is capable of producing anti-sense DHFR RNA which is complementary to the normal DHFR mRNA produced in the same cells. The anti-sense DHFR RNA can specifically hybridize to normal DHFR in the eukaryotic cell line and consequently, can increase both the MTX sensitivity and the desired protein production at lower MTX levels in these eukaryotic cells.

The above expression system of the invention may be used to control the expression of a desired protein selected from the group of desired proteins consisting of the known medically and veterinarily important proteins produced in CHO cells under DHFR/MTX regulation, for example, interleukins (ILs), interferons (IFNs), receptors and others.

Accordingly, the present invention provides an expression enhancing vector for regulating the expression of the normal DHFR gene carried by an eukaryotic cell line, the expression enhancing vector comprising:

a) a double stranded sequence encoding the DHFR gene or a portion thereof in the anti-sense or reverse orientation instead of the sense or normal orientation, the anti-sense DHFR sequence being transcribable by RNA polymerase under the control of a promoter sequence to yield an anti-sense RNA product that is complementary to the normal DHFR mRNA sequence or a portion thereof, and capable of specifically hybridizing to the normal DHFR mRNA sequence, sufficiently to inhibit translation of the normal DHFR mRNA;

b) a promoter sequence situated adjacent to the anti-sense DHFR sequence and controlling the expression of the anti-sense DHFR sequence. The promoter sequence is located upstream of the 5' end of the anti-sense DHFR sequence so that the 5'→3' directionality of the promoter sequence is in phase with the 5'→3' directionality of the anti-sense sequence enabling transcription to proceed from the promoter in the 5'→3' direction to yield an anti-sense DHFR RNA product; and, optionally, c) a genetic marker gene sequence encoding a product, the expression of which is readily screenable or selectable in cells transfected with and expressing the expression enhancing plasmid.

The present invention also provides a method for regulating the level of desired protein production in eukaryotic cells which comprises genetically manipulating an eukaryotic cell line so that it expresses a protein of interest, together with both DHFR (so that it is MTX-resistant) and an anti-sense DHFR RNA which hybridizes with normal DHFR mRNA to inhibit the translation thereof, thus leading to a decrease in DHFR production and in the level of inhibition of MTX. This decreased level of MTX-inhibition results in an increase in the amplification of the desired gene and its subsequent expression. In one embodiment this genetic manipulation involves:

a) constructing an eukaryotic cell line that is DHFR$^+$, MTX-resistant and capable of producing a desired protein, the level of production of which is at least partly regulated by the MTX-amplifiable copy number of the gene encoding the desired protein. (The level of MTX-induced amplification is regulated by the level of normal DHFR expression in these cells); and b) transfecting the eukaryotic cell line with an expression enhancing vector according to the present invention.

It will be appreciated, however, that the genetic elements (the gene encoding the protein of interest, the DHFR gene, and the anti-sense DHFR gene) can be introduced in any order, and on the same or different vectors, provided that the DHFR gene and the gene of interest are or become associated such that amplification of the DHFR gene results in amplification of the gene of interest.

The new expression system provides for both an increase in the amount of protein produced and a reduction in the cost of producing medically and veterinarily important proteins in CHO cell cultures.

The method of the present invention results in an increase in expression, which is to a level preferably at least about 200%, more preferably at least about 300%, most preferably at least about 500%, that achieved in control DHFR$^+$ cultures not transferred with the anti-sense sequence.

This method is generalizable to other gene amplification systems in which a directly amplifiable gene (the counterpart of the DHFR gene in our model system) whose expression product is required to protect the cell from a toxic agent (the counterpart of the methotrexate in our model system) is cotransfected with a gene of interest, which thereby becomes indirectly amplifiable by exposing the cell to the toxic agent. This exposure causes the cell to elevate expression of the protective expression product in such a manner as to result in the elevated expression of the gene of interest. The method would then involve expression of anti-sense RNA which inhibits translation of the mRNA encoded by the directly amplifiable gene so as to render the cell more sensitive to the elicitor.

Additional aspects and embodiments of the invention are set forth or readily arise from the drawings described below, or from the following detailed description of the preferred embodiments of the invention.

BRIEF DESCRIPTION OF THE DRAWINGS

For convenience, this figure has been subdivided into three parts.

DETAILED DESCRIPTION OF THE PREFERRED EMBODIMENTS OF THE INVENTION

Figures 1A, 1B:
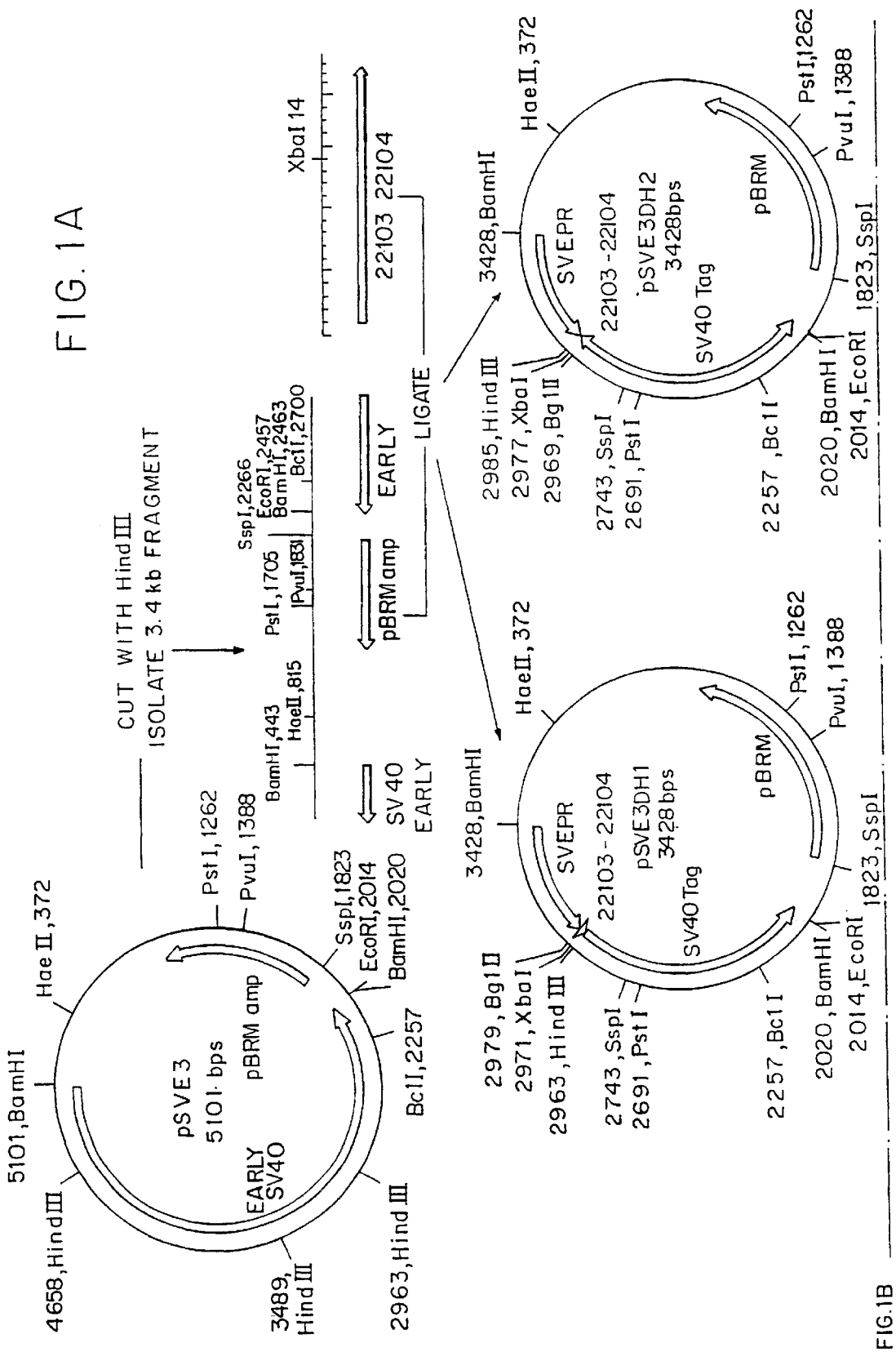
In FIG. 1(a), pSVE3DH1 and pSVE3DH2 are constructed, using pSVE3 as a starting material. Also, the DHFR gene is inserted into pSVE3DH1 in an antisense orientation to yield pSVEaDHFR.
In FIG. 1(b), the plasmid pSVEaDHFR is used as a starting material in the production of pSVEadHFR1 and pSVEadHRF2. Finally, in FIG. 1(c), plasmids pSVEadHFR1, pMAMneo and pSVEadHFR2 are used in the construction of a DHFR1/NeoR, a DHFR1/Neo, a DHFR1/NeoR, and a DHFR2/Neo (FIGS. 1(d)–1(h)).
Figure 1B:
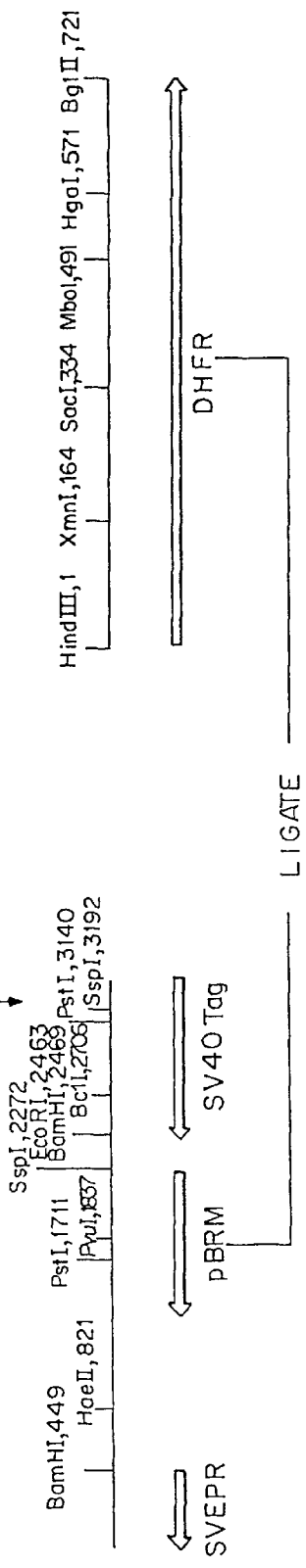
Figure 1B:
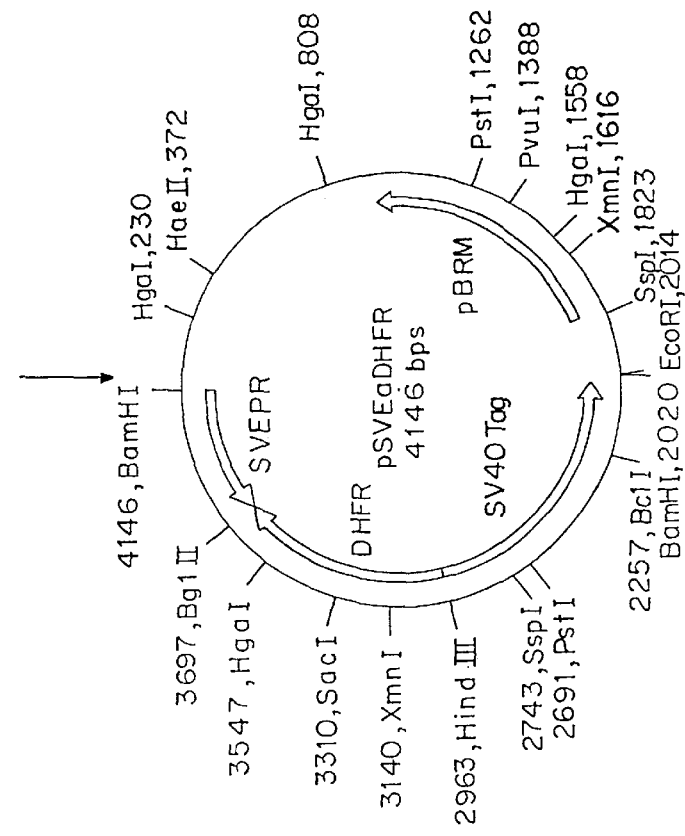
Figure 1D:
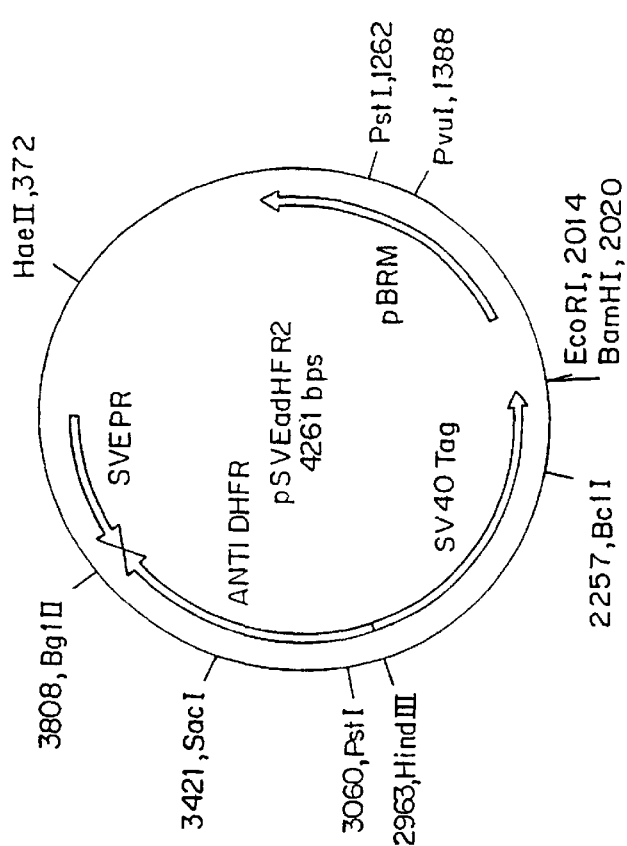
FIG. 1 is a schematic outline of the construction of the anti-sense DHFR-encoding plasmids showing the parent plasmids from which various regions were excised and subsequently ligated to provide the anti-sense DHFR-encoding plasmids, as described in Example 1.
Figure 1D:
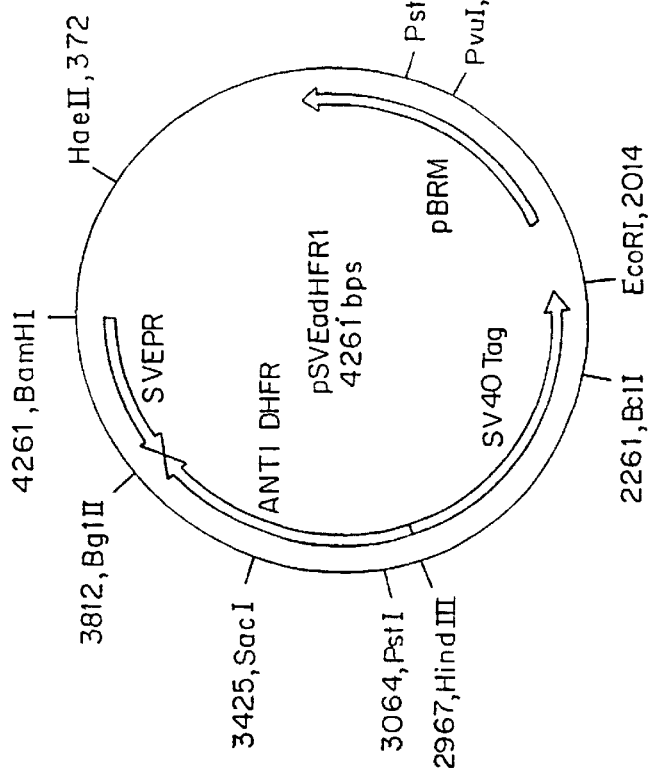
Figure 1G:
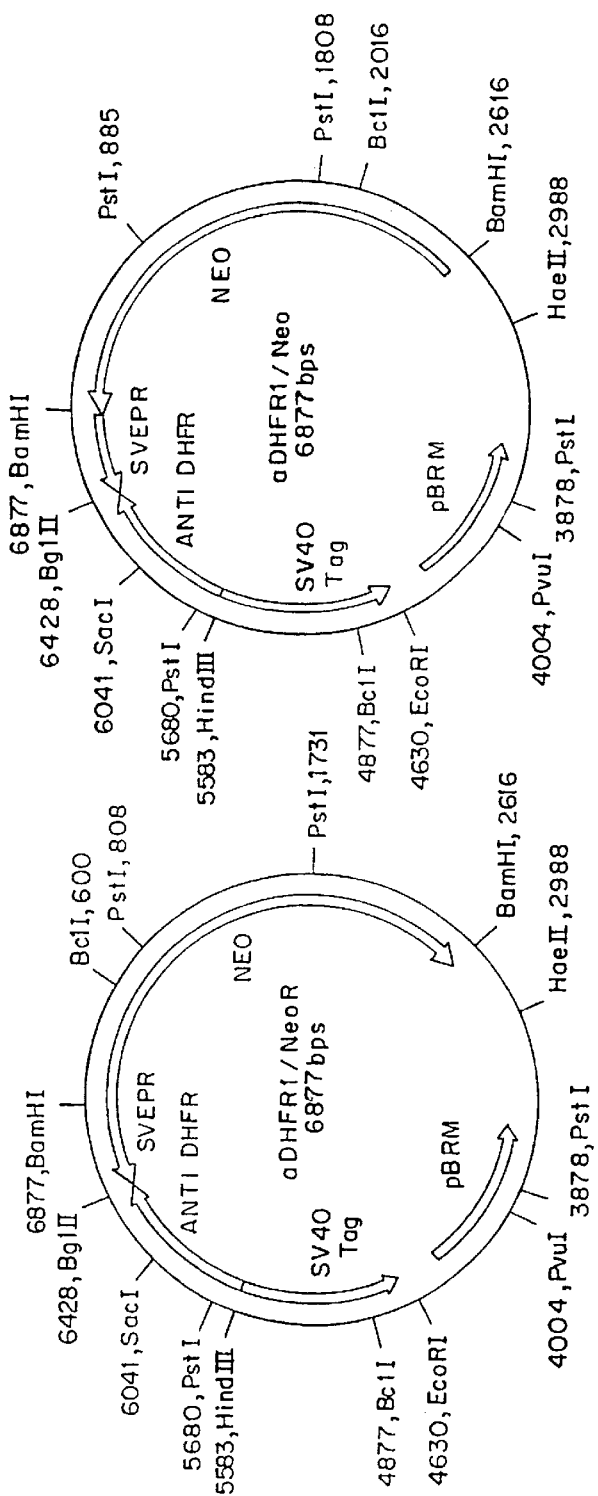
Figure 1H:
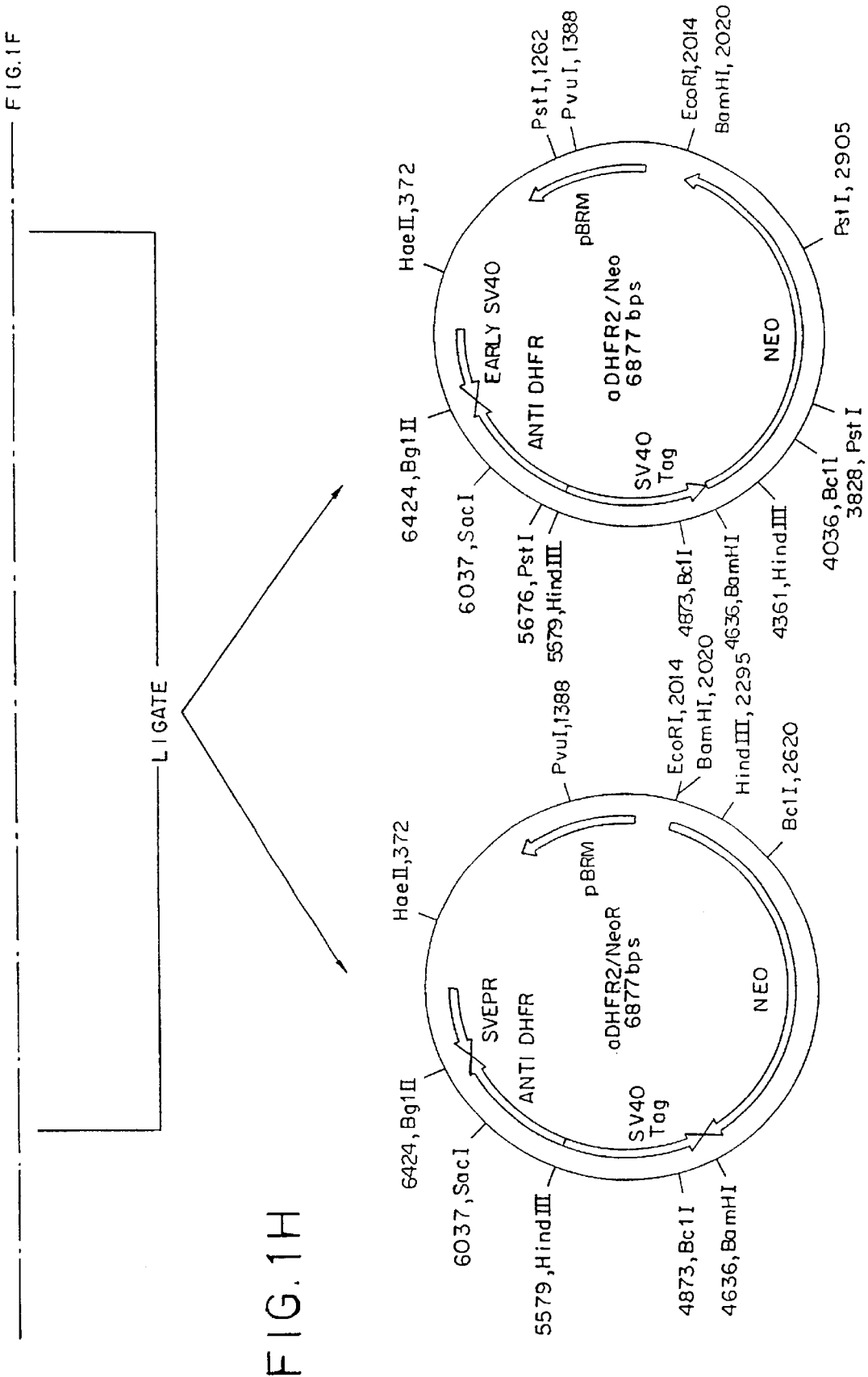
Figure 2:
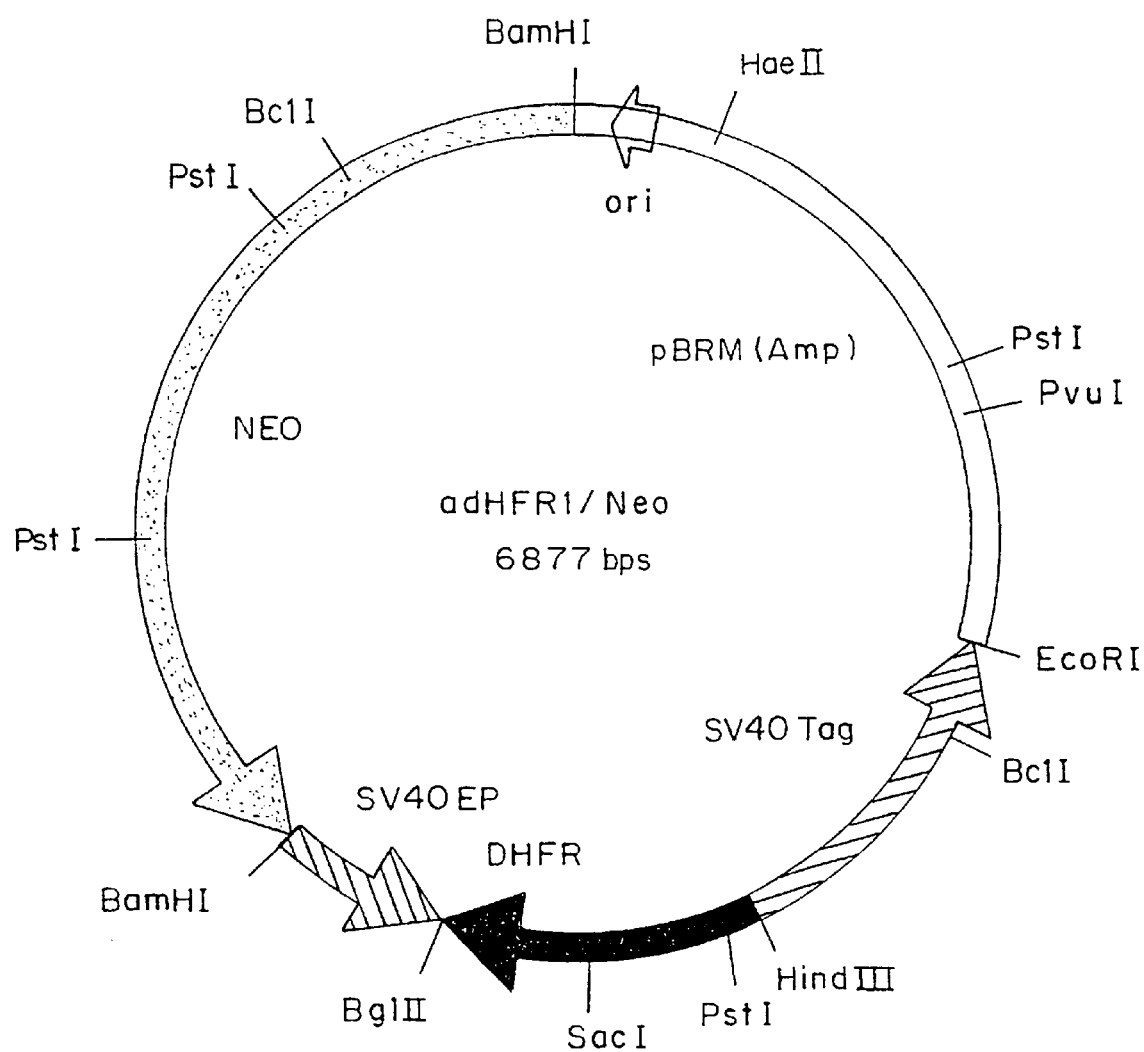
FIGS. 2–5 are schematic representations of the anti-sense DHFR-encoding plasmids in which the various arrowheads denote the orientation of various coding regions, each different coding region being denoted by a different pattern next to which appears the abbreviated name of the region, as described in Example 1.
Figure 3:
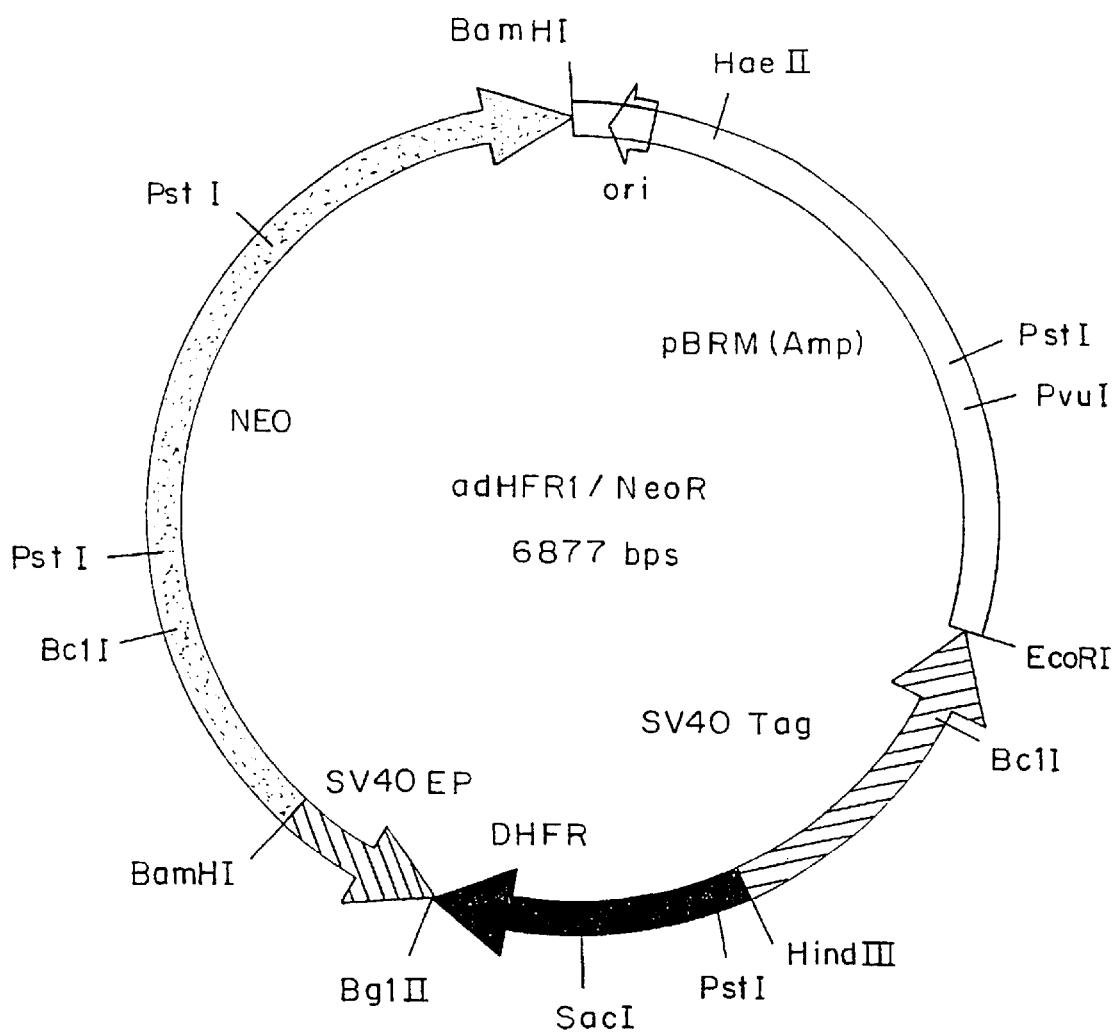

The present invention, in a preferred embodiment, concerns (1) an expression vector encoding an anti-sense DHFR sequence, (2) an expression enhancing system using this vector to regulate production of a desired protein in eukaryotic cell line, and (3) a method for regulating the production level of a desired protein in an eukaryotic cell line by transfecting these cells with the vector of the invention.

Cell lines transformed with the so-called "anti-sense DHFR" vector are, however, more sensitive to MTX than the original DHFR$^+$ cell lines because, upon expression of the anti-sense DHFR sequence, the translation of endogenous DHFR$^+$mRNA into the DHFR enzyme is blocked and the transformed cells become almost DHFR$^-$. Thus, for practical purposes, the selection of transformed cell lines selects those which still retain net DHFR$^+$ expression, i.e., where the expression of normal DHFR$^+$mNRA is greater than the newly-acquired anti-sense DHFR RNA expression.

Moreover, due to the decreased net DHFR$^+$ expression in these cells, the cells are also rendered more sensitive to MTX with the result that less MTX is required for gene amplification. Consequently, these anti-sense DHFR-expressing cells produce elevated levels of the desired protein as exemplified by some clones achieving a 500% higher expression level of the desired protein. This increase may be explained by the fact that addition of a small amount of MTX preferentially amplifies the DHFR$^+$ gene sequence and its flanking sequences (including the desired protein) in contrast to the anti-sense DHFR sequence which is either amplified to a lower extent or not at all. This difference in amplification results in an increase in net DHFR$^+$ expression as well as in net expression of the desired protein, which in turn allows for either the addition of more MTX, or maintenance of the original low MTX level without any associated toxic effects thereby leading to continued elevated expression levels of the desired protein. Thus, the balance between the expression of the DHFR$^+$ and anti-sense DHFR sequences which result in a net DHFR$^+$ has the overall effect of lowering the MTX needed for gene amplification and allowing for the addition of more and more MTX to achieve even higher levels of gene amplification beyond the levels obtained prior to transformation/transfection with a vector carrying an anti-sense DHFR sequence. In this way, the upper limit for the amount of desired protein that can be expressed can be greatly increased.

The vectors of the invention were constructed using standard methods of molecular genetics (Sambrook et al. Molecular Cloning, 2nd edition, Cold Spring Harbor Laboratory Press, Cold Spring Harbor, N.Y. (1989)), and used to transfect DHFR$^+$, MTX-resistant CHO cell lines which also produce a desired protein. Some of the resulting clones (see Examples 1 and 2) which were rendered more MTX-sensitive were capable of producing significantly elevated amounts of the desired protein, i.e. specific productivity was increased (in some cases up to 5-fold or 500% more).

As with the amplifiable DHFR gene, the present method for increasing the responsiveness of an amplifiable gene to a toxic agent such as methotrexate is generalizable to other gene amplification systems such as those listed in Table 1 of Kaufman, op. cit., herein incorporated by reference. For instance, ornithine decarboxylase (ODC) is an amplifiable gene selectable with increasing concentrations of the suicide-substrate inhibitor difluoromethylornithine (DFMO). Example 3 hypothetically shows how anti-sense ODC DNA can be expressed in transformed cells to increase the responsiveness of the cell to added DFMO in regulating the level of DFMO-amplified copy number of the gene encoding the desired protein. Anti-sense ODC RNA expressed from transformed cells will also selectively hybridize to ODC mRNA, reducing the level of ODC enzyme produced and thereby increasing the responsiveness of the transformed cells to DFMO.

Vectors

While vectors of the invention may be any suitable eukaryotic or prokaryotic vector normally used for transfecting eukaryotic cells such as CHO cells (see Sambrook et al., chapters 1, 2, 3 and 16, op. cit. for some examples of known vectors used for transfecting eukaryotic cells), plasmids are the most preferred vectors for carrying the anti-sense DNA sequence that acts to control expression of DHFR and the desired protein of interest.

The plasmid vectors of the invention were constructed to contain the following key elements: an anti-sense DHFR sequence; an efficient promoter adjacent to the anti-sense DHFR sequence and positioned with respect to the anti-sense DHFR sequence in such a way that only anti-sense DHFR mRNA can be transcribed by a RNA polymerase initiating transcription from that promoter; and a selectable genetic marker other than the normal DHFR gene, such as an antibiotic resistance-encoding gene sequence, which allows for the rapid selection of those CHO cells transfected by the plasmid vector of the invention. This selection is simply achieved by growing the cells in the presence of the antibiotic where successfully transfected cells are being protected by the antibiotic resistance-encoding sequence. The "normal" DHFR gene may be on the same or a different vector from the antisense DHFR gene, or it may be a native element of a chromosome of the host cell. Normally, the cell will be already DHFR+ and then transformed with an anti-DHFR vector.

The "Normal" DHFR Gene and Polypeptide

The "normal" DHFR gene will be expressed, in a suitable host cell, to produce a DHFR polypeptide. Expression comprises transcription of the gene, resulting in production of a messenger RNA; followed by translation of the messenger RNA transcript, resulting in production of the encoded DHFR polypeptide. The DHFR polypeptide may also feature post-translational modifications. The anti-sense DHFR can inhibit expression by hybridizing to the gene, thereby inhibiting transcription, and/or to the messenger RNA, thereby inhibiting translation.

The term "normal DHFR gene" is intended to include any gene which encodes a DHFR polypeptide, as later defined. The term "normal" is used for contrast with "anti-sense", and not to indicate identity with a natural DHFR gene.

The DHFR coding sequence may be that of a DHFR gene which occurs in nature. It may also be advantageous to modify the DHFR DNA sequences, e.g., to "silently" mutate degenerate codons to improve stability, reduce RNA secondary structure formation or raise the melting temperature ($T_M$) of the annealed DHFR mRNA and anti-sense DHFR RNA. By mutating degenerate codons, the nucleotide sequence of the DHFR gene and its complementary anti-sense DHFR sequence can be modified without modifying the amino acid sequence of DHFR. Any modification to the DHFR DNA coding sequence would normally mean a corresponding modification of the anti-sense DHFR DNA coding sequence in order to maintain complementarity between the sense (normal) and anti-sense DHFR sequences. However, as elsewhere mentioned, the greater the number of complementary base pairs, the greater the number of non-complementary bases that can be tolerated, especially if the non-complementary bases are scattered.

As an example, the GC content of the DHFR and anti-DHFR genes can be increased in a complementary manner to raise the $T_M$ of the annealed DHFR mRNA/anti-sense DHFR RNA, thereby providing further stability to the annealing of anti-sense DHFR RNA to DHFR mRNA in the inhibition of DHFR translation.

Sequence modification can also be used to reduce secondary structure formation by self-annealing of DHFR mRNA. For instance, degenerate codons can be used to replace specific codons of the DHFR sequence which disrupt RNA secondary structure by preventing self-annealing through selective elimination of complementary bases that give rise to secondary structure. The choice of specific nucleotide(s) to modify in the DHFR sequence can be determined from an estimation of the DHFR mRNA secondary structure using RNA estimation techniques reported in, for example, Tinoco et al., Nature New Biology 246:40–41 (1973), Tinoco et al., Nature 230:362–367 (1971), and Bachra J. Mol. Emol. 8:155–173 (1976).

The DHFR gene may also be non-silently modified, i.e., so that a mutant DHFR polypeptide, of greater or lesser enzymatic activity, is produced, provided that the polypeptide is still capable of imparting, at its level of expression, sufficient resistance to methotrexate so that the gene of interest is amplified.

A "DHFR polypeptide" is any DHFR form which occurs in nature, or a mutant (including a fragment or chimera) which is substantially identical to a natural DHFR (preferably a mammalian DHFR), and retains at least 10% of the native DHFR activity of the most homologous native DHFR.

The DHFR may be a DHFR polypeptide which occurs in nature, or a mutant thereof, especially one obtained by conservative substitution of amino acids. Many DHFRs have been sequenced, and the relative importance of residues may be ascertained by aligning the sequences, with residues important to activity being more strongly conserved. Substitution of amino acids with others of similar size, hydrophobicity and charge, or amino acids found at that position in other DHFR, is less likely to perturb activity. The DHFR is preferably a mammalian DHFR, especially a mouse DHFR. The sequence of the mouse DHFR is cited in the examples.

Anti-Sense DHFR

The anti-sense DHFR sequence must not only be expressible in the host/target cells, but the expressed anti-sense RNA must be stable (i.e., does not undergo rapid degradation). Moreover, the anti-sense DHFR RNA, will essentially specifically only hybridize to the sense DHFR mRNA expressed in host cells, and form a stable double-stranded RNA molecule that is essentially non-translatable. In other words, the anti-sense DHFR RNA expressed in transfected host cells prevents the expressed sense DHFR mRNA from being translated into active DHFR enzyme. The vector-borne anti-sense DHFR sequence may carry either the entire DHFR gene sequence or merely a portion thereof as long as the anti-sense DHFR sequence is capable of hybridizing to "sense" DHFR mRNA and preventing its translation into DHFR enzyme. Accordingly, an "anti-sense" sequence of the invention can be defined as a sequence which is capable of being expressed in transformed/ transfected cells and which is also capable of specifically hybridizing to "sense" DHFR mRNA to form a non-translatable double-stranded RNA molecule.

The anti-sense DHFR sequence need not hybridize to the entire length of the DHFR mRNA. Instead, it may hybridize to selected regions, such as the 5'-untranslated sequence, the coding sequence, or the 3'-untranslated sequence of the "sense" mRNA. In view of the size of the mammalian genome, the anti-sense DHFR sequence is preferably at least 17, more preferably at least 30, base pairs in length. However, shorter sequences may still be useful, i.e., they either fortuitously do not hybridize to other mammalian sequences, or such "cross-hybridization" does not interfere with the metabolism of the cell in a manner and to a degree which prevents the accomplishment of the objects of this invention.

Both the preferred hybridization target and the preferred anti-sense sequence length are readily determined by systematic experiment.

Standard methods such as described in Sambrook et al., 1989 can be used to systematically remove an increasingly larger portion of the anti-sense DHFR sequence from the plasmid vector. Besides the full length anti-sense DHFR sequence, a series of staggered deletions may be generated, preferably at the 5'-end of the anti-sense DHFR sequence. This creates a set of truncated anti-sense DHFR sequences that still remain complementary to preferably the 5'-end of the sense DHFR mRNA and as a result, still forms a RNA molecule that is double-stranded at the 5'-end of the sense DHFR mRNA (complements the 3'-end of an anti-sense DHFR RNA) and remains non-translatable. Since the DHFR$^+$ enzyme product is essential to cells, the level of anti-sense inhibition can be readily determined by either measuring cell viability (complete DHFR$^+$ inhibition causes cell death when grown in unsupplemented standard medium) or sensitivity to MTX. Thus, the series of plasmid vectors generated by staggered deletions of anti-sense DHFR sequence, each having a different modified anti-sense sequence, can then subsequently be tested for their effectivity in DHFR$^+$ host cells. In this way, plasmid vectors containing a range of truncated anti-sense sequences can be obtained and used individually or in combination as expression control vectors for amplifying the protein of choice as well as the DHFR$^+$ marker.

It is not necessary to use a single antisense DHFR. Different antisense molecules, each targeting a different segment of the target gene, may be used jointly. See Macher III and Dolnick, Nucelic Acids Res., 16:3341 (1988).

Promoters (for Expression of Anti-Sense Sequence)

The types of promoters used to control transcription of the anti-sense gene to yield the anti-sense RNA may be any of those which are functional in the host cells. Examples of promoters functional in mammalian cells include the SV40 early promoter, adenovirus major late promoter, herpes simplex (HSV) thymidine kinase promoter, rous sarcoma (RSV) LTR promoter, human cytomegalovirus (CMV) immediate early promoter, mouse mammary tumor virus (MMTV) LTR promoter, interferon β promoter, heat shock protein 70 (hsp70) promoter, as well as many others well known in the art.

These promoters may be either constitutive or regulatable. All else being equal, constitutive promoters are preferred because an extra treatment step such as temperature shift, addition of chemical agents or inducers, etc., is not required for expression from constitutive promoters. Nonetheless, regulatable promoters may be desirable to modulate the level of anti-sense DHFR expression to maximize the degree of amplification. If the expression level is too high, the cells may not grow or even survive. If it is too low, the cells may not respond adequately to the methotrexate. When regulatable promoters are to be used for expressing the anti-sense sequence, it may be desirable to suitably modify the host cells to increase their tolerance to the inducing conditions used, e.g., temperature shifts.

Markers

The "marker" gene used to verify transformation of the cells with the anti-sense vector is preferably an antibiotic resistance gene. The types of antibiotic resistance sequences which may be carried by the vector may be any of the well known antibiotic resistance sequences, for example neomycin-resistance (or G418-resistance) and hygromycin resistance. Other screenable or selectable markers may be used instead of antibiotic resistance genes. In Kaufman R. J. (op. cit.), a review of gene selection in mammalian cells, providing a list of possible antibiotic resistance and other selectable markers such as markers involved in the salvage pathway for pyrine and pyrimidine biosynthesis which may be used in the vector of the present invention, is provided. For example, Table 1 of the Kaufman reference (op. cit.) shows that adenosine deaminase (ADA), one of many other selectable markers, can be selectable at cytotoxic concentrations of adenosine or 9-β-D-xylofuranosyl adenine.

Target Cells

The target cell may be any cell which, either naturally or, as a result of genetic manipulation, is DHFR$^+$. CHO cells are preferred as the target cells of the invention because well-characterized DHFR$^-$ CHO cell lines which are easily and readily transformed to DHFR$^+$ are available. Moreover, CHO cell lines are widely used for the industrial production of a variety of mammalian proteins and culture requirements are well established. Other well-known eukaryotic cell lines such as mammalian, yeast and insect cell lines may be used in the expression system of the invention if suitably modified in a similar manner as the CHO cell lines. However, mammalian cell lines, and especially CHO cells, remain preferred.

Preferably, a DHFR$^-$ cell line is established first, and then transformed/transfected with a vector carrying both the DHFR$^+$ gene sequence and a gene encoding the protein of choice. Positive transformants are selected by growing the transformed/transfected cells in a basic minimal culture medium such that only those cells expressing the essential DHFR enzyme (DHFR$^+$ cells) will survive. Before amplifying with MTX, the DHFR$^+$ transformed cell lines would need to be tested for the level of MTX-resistance, whether MTX-induced amplification is effective, and whether anti-sense DHFR regulation is necessary for further increases in expression of the desired protein.

It is preferable that the DHFR gene sequence be incorporated into the genome upon transformation/transfection to ensure that the transformants stably and constitutively express the essential DHFR enzyme. In addition, the gene encoding the protein of choice is stably co-integrated into the genome with the DHFR gene sequence with the protein of choice being expressed in either a constitutive or regulatable manner.

Transformation

The anti-sense DHFR sequence, carried on a separate selectable vector, may be introduced into cells by any of well-known techniques for transforming/transfecting eukaryotic cells, such as electroporation, calcium phosphate treatment, and liposome-mediated transformation, etc. (see Ausubel et al. CURRENT PROTOCOLS IN MOLECULAR BIOLOGY, Greene Publishing Assoc., New York (1987–1994) chapter 9) and maintained in cells either via stable integration into the cell genome or on a non-integrated vector. If integration is desired, then it must be ensured that not only does integration of the anti-sense sequence not lead to loss of the sense DHFR$^+$ sequence, but that once integrated, the anti-sense DHFR sequence is still expressed.

While it is preferable to transform DHFR$^+$ cells, which have both DHFR and the gene of interest integrated into the genome, with anti-sense DHFR DNA, a different order of introducing the various sequences is also contemplated. As an example of another possible order to constructing a production cell line for the protein of interest, the anti-sense DHFR DNA along with a selectable marker can be introduced first into the genome followed later by the introduction and integration of the DHFR group together with the gene of interest into the genome. Again, it must be ensured that integration of the DHFR gene and the gene of interest does not lead to lose of the anti-sense DHFR sequence. With this particular order of gene transformation, the anti-sense DNA is preferably expressed from a regulatable promoter so that prior to a first series of DHFR/gene of interest amplification with methotrexate, there is no expression of anti-sense DNA. This would allow the copy number of DHFR/gene of interest to be first amplified prior to increasing the responsiveness to further amplification with methotrexate. The two different order of introducing sequences described above are non-limiting examples, other possibilities can be readily devised based on the disclosure presented herein.

Protein of Choice

With respect to gene amplification of the target cells prior to introducing the expression enhancing vector of the invention, both the DHFR$^+$ gene and the co-integrated protein of choice gene, which flanks the DHFR$^+$ gene, are amplified together. The protein of choice can be any protein having pharmaceutical, veterinary or industrial importance that is currently being produced or can be produced. This includes a long list of proteins (including polypeptide hormones) which can be categorized as follows:

a) Pharmaceutically important proteins/hormones: (i) cytokines and cytokine receptors such as interleukins (IL-1, IL-2, IL-6, etc.) and their receptors; interferons (IFN-α, -β, -γ, etc.) and their receptors (RBIF, etc.); tumor necrosis factors (TNF-α, -β, etc.) and their receptors (TBP-1, TBP-2); (ii) hormones for growth regulation of the reproductive system, regulation of the circulatory (blood) system and regulation of the nervous system, e.g., all the various growth factors, GH, aFGF, bFGF, KGF and their receptors; FSH, LH, CG and their receptors; erythropoietin (EP), plasminogen activator (tPA), the various platelet factors (blood clotting agents) and their receptors; the various neurotransmitters, neuro-hormones, e.g., ACHE, BCHE, serotonin, etc. and their receptors, (iii) the various proteins, enzymes, factors involved in malignant growth regulation, e.g., the various oncogene products, etc., the various hormones involved in regulation of carbohydrate metabolism and uptake, e.g., insulin, glucagon, etc., and their receptors. Factors/proteins involved in all kinds of disease, e.g., multiple sclerosis, muscular dystrophy, etc., are also included in the above list.

b) Veterinarily important proteins: As above, i.e., all proteins, growth factors, hormones, etc., which are produced for administration to animals for maintaining or improving their well-being or for increasing their size or milk production, etc.

c) Industrially important proteins: Includes all enzymes/proteins that are produced for applications in fermentation processes, fiber-production processes, cheese-making processes, etc.

The promoter used for expressing the protein of choice can be the native promoter for the gene encoding the desired protein or it can be any suitable promoter capable of expressing the desired protein, preferably at high levels. The promoter can be constitutive or regulatable and can be any one of those currently used in mammalian expression systems as described above for promoters expressing the anti-sense sequence. It should be noted that the promoter used for expressing the desired protein may be different from the one used to express the anti-sense DHFR or it may be the same. However, if the expression of the anti-sense DHFR is to be regulatable, i.e., so as to assure net DHFR expression over anti-sense DHFR expression sufficient for cell growth and survival, then the promoter for the gene encoding the desired protein is preferably different from the promoter for expressing anti-sense DHFR.

Culture Conditions

The culture conditions used for culturing the CHO cells were the standard culture conditions generally used for CHO DHFR$^+$ cells that are treated with MTX (see Kaufman, R. J., Methods in Enzymol., 185, 537–566 (1990)). If other cells are used, the culture conditions may be whatever is suitable for growth of said cells and compatible with gene amplification as disclosed herein.

The invention will now be described in more detail in the following non-limiting examples and their accompanying figures.

EXAMPLE 1

Construction and Characterization of Plasmids Encoding an Anti-sense DHFR Sequence (A) Plasmid Construction Plasmids containing the murine DHFR gene (see Chang, et al., Nature, 275:617–24 (1978) and Genbank sequences J00382, J00383, J00384, J00385, J00386, J00387, J00388; L26316; NCBI sequence 387160) in the anti-sense orientation were constructed with an antibiotic resistance gene as an additional selectable genetic marker. This additional selectable marker is necessary since the plasmids encoding the anti-sense DHFR sequence are intended for transfection of CHO cells already transfected with the normal DHFR gene. While the most suitable antibiotic-resistance genes for this additional selectable marker are those encoding hygromycin B or neomycin (G418) resistance, other antibiotic resistance genes may be used under the condition that their expression in CHO host cells do not cause cell death or interfere with the gene amplification mechanism.

The antibiotic resistance marker is preferably G418, with this preferred marker being inserted into the various anti-sense DHFR-encoding plasmids.

A schematic outline of how anti-sense DHFR-encoding plasmids carrying the G418 resistance marker were constructed from pre-existing (parent) plasmids is set forth in FIGS. 1(a)–(c). The methods used for constructing these plasmids are the well-established methods of molecular genetics/genetic engineering (see Sambrook et al., op cit.).

Some of the genetic elements used in the constructions illustrated in FIG. 1 are discussed below; they are all well known in the art.

pBRM is a 2 kb fragment of pBR322, containing the β-lactamase gene conferring resistance to ampicillin, and the plasmid origin of replication. The incorporation of the pBRM fragment into a mammalian expression vector makes possible the propagation of the plasmid in E. coli. Of course, one may use a different origin of replication to achieve the same objective. See Sutcliffe, J. G. (1979) Cold Spring Harbor Symp. Quant. Biol. 43:77–90.

"SV40 Tag" is the coding region for SV40 T Antigen, located in the early region of SV40, between SV40 early promoter and polyadenylation sequences. See Tooze, J. (ed.) (1980) DNA Tumor Viruses: Molecular Biology of Tumor Viruses. (Cold Spring Harbor Laboratory, Cold Spring Harbor, N.Y.) Part 2.

pSVE3 is an expression vector contains pBRM and the whole early region of SV40 (Tag). In the paper which summarizes the construction of pSVE3, a description of its components is given. See Hartman, J. R. et al. (1982) Proc. Natl. Acad. Sci. USA 79:233–237.

PR22103 and PR22104 are both oligonucleotides of 22 bases long each, which combine to give an adaptor fragment, used in the first step of construction of the plasmid containing DHFR sequence in pSVE3.

PR22103 5' AGCTCAGATC TCGTCTAGAG GA 3' (SEQ ID NO:1)

PR22104 3' GTCTAG AGCAGATCTC CTTCGA 5' (SEQ ID NO:2)

pMLMneo is a mammalian expression vector (Clontech). The Neomycin resistance gene was removed from pMAM-neo and introduced into antisense-DHFR plasmids, in order to enable selection of cells carrying this plasmid. See Lee, F., et al. (1981) Nature 294:228.

The structure of the plasmids was characterized by restriction map analysis.

Four different anti-sense DHFR plasmids were obtained by the above standard procedures and are depicted schematically in FIGS. 2–5, which show the restriction and sequence orientation maps of these plasmids.

Figure 4:
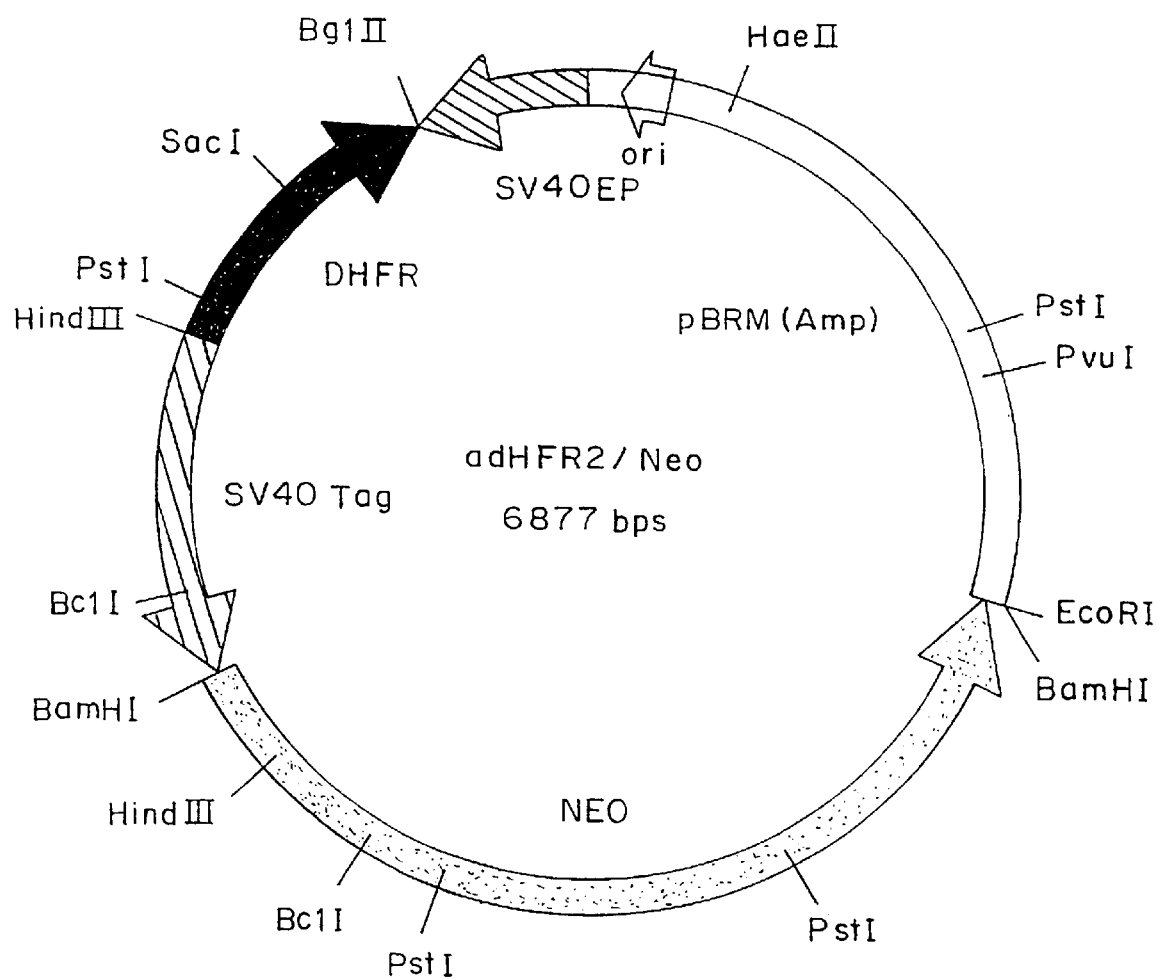
Figure 5:
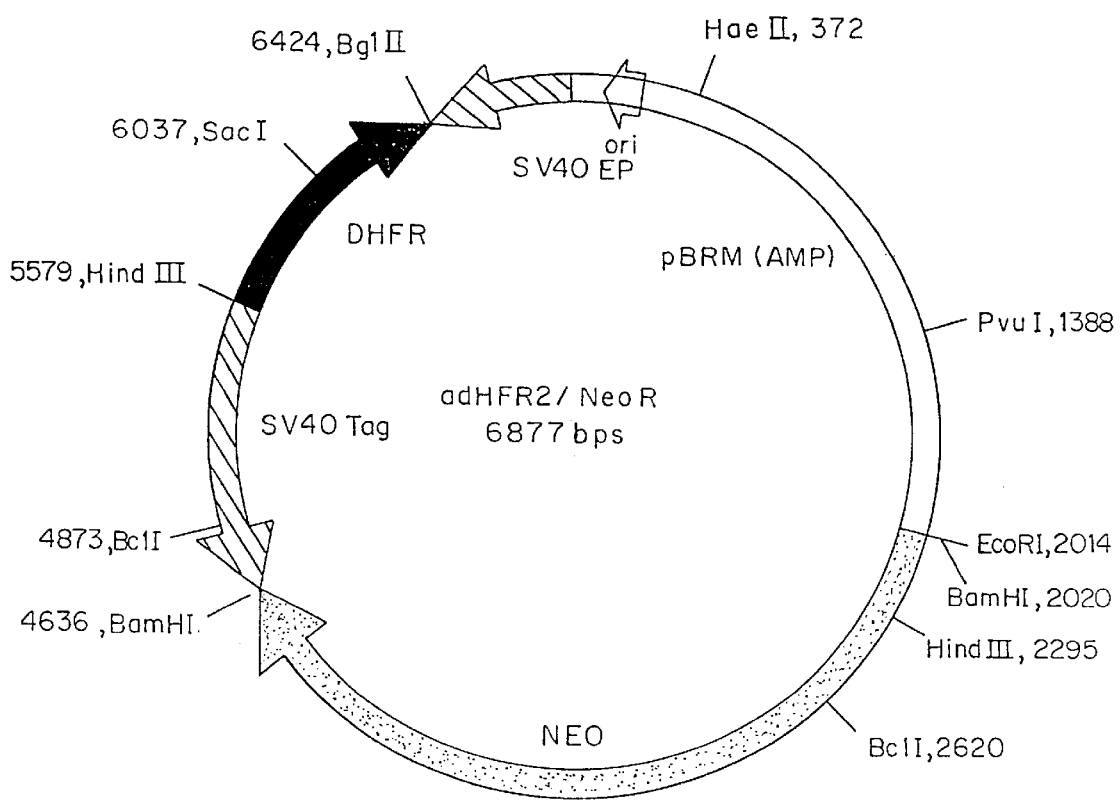

The four plasmids were designated: adHFR1/Neo (FIG. 2); adHFR1/NeoR (FIG. 3); adHFR2/Neo (FIG. 4), and adHFR2/NeoR (FIG. 5). The difference between the four plasmids resides in the position of the neomycin resistance gene, 5' (upstream) or 3' (downstream) in relation to the anti-sense DHFR gene and in the orientation of the neomycin resistance gene with respect to the orientation of the anti-sense DHFR gene. The neomycin resistance gene confers resistance to G418 and converts host cells to G418-resistant cell lines. Each of the four plasmids have a length of 6877 base pairs (bps) and contain the following regions: NEO=neomycin-resistance gene; pBRM(Amp)=ampicillin-resistance coding region derived from pBR322-type plasmids; SV40 Tag=sequence of the SV40 viral genome encoding the T-antigen of SV40; SV40 EP=SV40 virus-derived early promoter; DHFR=anti-sense DHFR gene; and ori= origin of plasmid replication, also of pBR322-type plasmid origin. As illustrated in FIGS. 2–5, the anti-sense DHFR sequence is located between the SV40 early promoter (i.e. this DHFR sequence is under the control of the SV40 early promoter) and T-antigen sequences, i.e. the anti-sense DHFR sequence was inserted into the SV40 EP/Tag region of the parent plasmid (see FIG. 1) between the BglII and HindIII restriction enzyme sites. The 5'–3'orientation of the DHFR sequence is reversed with respect to the SV40 EP/Tag sequence, and hence, when expressed, this DHFR sequence will be the "reverse" sequence of this gene, namely, an anti-sense sequence. Accordingly, the expressed anti-sense DHFR RNA sequence will be complementary to the normally expressed (in the CHO cells) DHFR mRNA (DHFR sense mRNA sequence), with the result that when expressed in the same cell these sequences will hybridize to each other, thereby effectively inhibiting the translation of the normal DHFR mRNA.

The above four anti-sense DHFR plasmids were tested for their ability to transfect, as secondary transfections, CHO clones that were transfected previously and presently expressing normal murine DHFR (DHFR$^+$ clones) and a desired protein, TBP-I (a soluble TNF receptor molecule). These tests were directed toward determining whether the transfected CHO clones are rendered sensitive to MTX since the expression of normal DHFR in these cells should be significantly inhibited following expression of the anti-sense DHFR sequence, thus causing the cells to be more responsive, or sensitive to MTX.

All of the above plasmids were shown to be equivalent in their ability to transfect CHO cells and in their ability to express the neomycin and anti-sense DHFR sequences. For illustrative purposes, the results of only one of these plasmids, adHFR2/Neo (FIG. 4) are set forth herein.

(B) Resistance to Neamycin

In order to determine the optimum plasmid concentration to be employed for the secondary transfections of CHO clones which produce TBP-I, e.g., the SBP13-30 CHO clone, cells of these clones were transfected with a range of anti-sense DHFR plasmids concentrations, each group of cells being transfected with a different plasmid concentration and compared with control cells not transfected with plasmid DNA.

Cells of CHO clone SBP13-30 (a DHFR$^+$ TBP-I producer) were transfected with increasing concentrations of anti-sense DHFR plasmid adHDR2/Neo. Equal amounts of cells were transfected with different amounts of the plasmid (0=control, and 5, 20, 100, 300 and 500 μg plasmid DNA). Following transfection, the cells were grown in selective medium containing G418. When the cell death of the non-resistant control (0 μg plasmid DNA) cells was complete at about 10–15 days following transfection, the transfected cells were stained with crystal violet to visualize surviving cells. The cells were plated and grown on standard Petri plates containing standard CHO cell culture medium with added G418. There was a clear visual correlation between increasing amounts of plasmid DNA used in transfection and the increase in number of neomycin-resistant cells.

The 0 μg DNA plate was unstained, the 5 μg plate was lightly stained, the 20 μg plate was moderately stained, the 100 μg and 300 μg plates were heavily stained, and there was a slight falloff on the 500 μg plate. It should be noted, however, that the optimal amount of plasmid DNA for cell transfections appears to be about 100 μg. This level provides the highest number of G418-resistant cells with higher DNA amounts not significantly increasing the number of surviving cells. From these results it is clear that the cells are successfully transfected with the plasmid and that the plasmid is expressed, i.e., expression of the neomycin resistance gene.

(C) Acquired Sensitivity to MTX

In order to assess the level of expression of the anti-sense DHFR sequence and whether its expression effectively blocks DHFR+ expression i.e. renders the cells more responsive/sensitive to MTX treatment, SBP13-30 CHO cells subjected to transfections with three different plasmid concentrations of adHFR2/Neo 0 (control), 100 and 500 μg plasmid DNA, were grown in the absence (controls) or in the presence of MTX (9 μM). Equal amounts of cells from each of the transfections were plated onto duplicate sets of Petri dishes containing standard CHO culture medium, one set receiving cells treated with MTX and the other set receiving untreated cells. When the cells in the dishes without MTX approached confluent growth, the experiment was terminated and the surviving cells were visualized by staining with crystal violet.

As expected, with 0 μM MTX, heavy staining was observed. The staining was moderate-to-heavy in the 9 μM MTX/0 μg DNA dish. The level of staining decreased as the amount of DNA was increased, the 500 μg DNA/9 μM MTX being lightly stained. Cells transfected with high amounts of plasmid (500 μg plasmid DNA/dish) are more sensitive to MTX than cells transfected with lower amounts of plasmid (100 μg plasmid DNA/dish) or the non-transfected control cells (0 μg plasmid/dish). Thus, it is clear that the anti-sense DHFR plasmid successfully transfected the CHO cells and was expressed in these cells. The results show that a higher amount of anti-sense DHFR plasmid per cell (per dish) used for transfection resulted in increased inhibition of DHFR$^+$ expression and hence, increased MTX sensitivity, i.e., the 9 μM concentration of MTX to which the cells of CHO clone SBP13-30 are normally resistant, becomes a toxic concentration in cells in which DHFR$^+$ expression is inhibited. In other words, the greater the DHFR$^+$ inhibition, the greater the MTX toxicity.

EXAMPLE 2

Isolation and Characterization of TBP-I-producing CHO Clones Transfected with an Anti-sense DHFR Plasmid Having Increased MTX Sensitivity and Higher Levels of TBP-I Production (A) Transfection of TBP-I Producing Clones with an Anti-sense DHFR Plasmid Two CHO clones, SBV14-24 and SK-108-1-22-12, producing TBP-I were transfected with the anti-sense DHFR clone, adHFR2/Neo (FIG. 4). CHO clone SBV14-24, a stable TBP-I producer, was isolated by one approach where, after several rounds of MTX selection, clone SBV14-24 was found to be highly resistant to MTX, at least up to the relatively high level of 10 μM MTX, a level which is usually toxic to CHO cells. CHO clone SK-108-1-22-12, was isolated using a second approach where selection was carried out at lower MTX levels (1.2 μM), resulting in clone SK-108-1-22-12 apparently having fewer copies of the normal DHFR gene, thus making those fewer copies more readily neutralized by the expression of the anti-sense DHFR plasmid.

Clone SBV14-24 was transfected with 30, 100 and 300 μg, respectively, of the above anti-sense DHFR plasmid, and the resulting neomycin-resistant clones were isolated and subjected to a MTX-sensitivity test. The isolated neomycin-resistant clones were then grown under standard CHO cell culture conditions, in which the cells of each clone were grown in two of the wells of a six-well Costar culture plate in standard CHO-cell-culture medium. 10 μM MTX was added to one of the two wells with the second well serving as a control (cells did not receive any MTX). Each Costar plate also had two additional control wells in which cells of the parental clones, i.e., non-transfected, non-neomycin resistant cells of the SBV14-24 clone, were grown. To one of these wells 10 μM MTX was added, while the other received no MTX. In much the same manner as described in Example 1 (C) above, when the cells in the wells without MTX grew to approach confluence, the experiment was terminated (this usually being after the cells were grown for a duration between several days and more than two weeks) and the surviving cells were stained with crystal violet for visualization (results not shown). Forty seven such neomycin resistant clones were tested, some of which showed no sensitivity to 10 μM MTX, i.e., behaving similarly to the parental clones which are resistant to 10 μM MTX. Other clones, for example, the ones designated 30d13 and 30d16 (the "30" denoting the amount of plasmid DNA, 30 μM, used for transfection) showed intermediate sensitivity to 10 μM MTX. A third group of clones, for example, the ones designated 30d15, 30d17, 30d18, 30d19 and 30d20, showed a high level of sensitivity to 10 μM MTX; i.e., much reduced numbers of cells surviving after incubation in the presence of 10 μM MTX. These highly sensitive MTX clones thus represent those having the highest anti-sense DHFR plasmid transfection efficiency and anti-sense DHFR gene expression. These clones were selected for tests to ascertain the effect of the acquired MTX-sensitivity on TBP-I production in these clones.

In a similar fashion, clone SK-108-1-22-12 was transfected with 30 or 100 μg of the above-noted anti-sense DHFR plasmid. The resulting neomycin-resistant clones were isolated and subjected to a MTX-sensitivity test in 6-well Costar plates, in which the test-wells received 1.2 μM MTX and the other control wells being equivalent to those noted above, with the exception that the control parental line cells were of clone SK-108-1-22-12. Thirty-six such clones were tested (results not shown), some of which showed no sensitivity to 1.2 μM MTX much like the parental cells while others showed intermediate sensitivity, and a third group showed high sensitivity (i.e., low cell survival) to 1.2 μM MTX. Examples of this high-sensitivity group are clones designated 30k26, 20k31, 100k01 and 100k11 ("30" and "100" denoting the amount of plasmid DNA used in the transfections, 30 μg and 100 μg, respectively). These high-sensitivity clones are those most efficiently transfected by the plasmid and which express the highest levels of the anti-sense DHFR gene. These clones were selected for tests to ascertain the effect of the acquired MTX-sensitivity on TBP-I production in these clones.

(B) Specific Productivity of TBP-I in the Selected MTX-sensitive Clones Derived from Parental CHO Clone SBV14-24

The specific productivity of parental clone SBV14-24 was measured by a standard ELISA procedure, specific for detection of quantification of TBP-I production. This ELISA procedure was carried out over a period of 5–16 months to ascertain the stability of this clone for TBP-I production. Over this period, the average specific productivity of this clone was calculated to be 7.25±1.82 μg/10$^6$ cells/24 hours.

The culture procedures used were as follows: The clone was grown in Petri dishes in standard CHO culture medium under standard CHO culture conditions with or without the addition of MTX. One day before the ELISA the medium was changed to fresh medium and the cells were incubated for a further 24 hours. The TBP-I production was measured in aliquots of the cell supernatants. Cell numbers in each culture were determined following trypsinization. TBP-I production was calculated per 10$^6$ cells, as well as per 24 hour culture, with the calculated value representing the specific productivity. The above noted neomycin-resistant anti-sense DHFR-transfected SBV14-24 clones having high MTX sensitivity were subjected to the same ELISA procedure over a two-month period. The clones having the highest TBP-I specific productivities are listed in Table 1 below. It should be noted that clones designated with names beginning with "30d", "100d" and "300d" are those in which the transfections were with 30 μg, 10 μkg, and 300 μg, respectively, of plasmid DNA.

From the results presented in Table 1, it is apparent that upon transfection with the anti-sense DHFR plasmid, TBP-I specific productivity remains at levels comparable to that of the parent clone SBV14-24, i.e., at or near 7.25±1.82 μg/10$^6$ cells/24 hours. Accordingly, the results indicate that transfection with the anti-sense DHFR plasmid did not affect the gene copy number of the TBP-I gene in these clones. The reduction in MTX resistance (acquired MTX-sensitivity) in these clones is due to translation inhibition of the normal DHFR mRNA by the anti-sense DHFR mRNA.

TABLE 1

Specific Productivity of Anti-sense DHFR clones derived from Clone SBV14-24

| Clone | Specific Productivity |
|---|---|
| 100d08 | 8.48 |
| 100d08 | 5.59 |
| 100d12 | 8.35 |
| 100d12 | 4.71 |
| 100d13 | 1.77 |
| 100d13 | 1.24 |
| 100d13 | 1.49 |
| 100d16 | 4.32 |
| 100d16 | 4.87 |
| 300d01 | 3.82 |
| 300d01 | 2.74 |
| 30d17 | 5.79 |
| 30d17 | 3.96 |
| 30d18 | 2.80 |
| 30d18 | 6.34 |
| 30d22 | 7.05 |
| 30d22 | 2.72 |

Based on MTX-sensitivity (intermediate to high) and the above noted TBP-I production of the above eight clones, these eight clones were selected for further gene amplification studies using MTX.

To carry out the gene amplification studies it was first necessary to determine the MTX concentration which caused 50–70% cell death in these clones. For each clone an MTX-sensitivity curve was determined (results not shown).

The cells of each clone were grown in each well of a six-well Costar plate in standard CHO culture medium and to each well was added a different concentration of MTX (0=control, 1 $\mu$M, 3 $\mu$, 5 $\mu$M, 7 $\mu$M and 10 $\mu$M. The cells were grown under standard CHO culture conditions for over two weeks and when, at this stage, the cells in the wells having received no MTX, had reached confluence, the cells were stained with crystal violet (results not shown). The results of this experiment indicated that clones 100d08, 100d12, 100d16, 300d01, 30d18 and 30d22, had intermediate MTX-sensitivity (4 $\mu$M–5 $\mu$M MTX) Accordingly, for further gene amplification studies, clones 100d08 and 100d16 were treated with 5 $\mu$M MTX, clone 100d12, 100d01, 10d18, 10d22 were treated with 4 $\mu$M MTX; clone 30d17 was treated with 3 $\mu$M and clone 100d13 was treated with 2 $\mu$M MTX. In these further gene amplification studies, clones were derived from each of the above MTX-treated clones and their specific productivities of TBP-I were measured by ELISA as above. In Tables 2–9 below, the results of the ELISA are shown; the values of specific productivity being average values obtained from a number of ELISA determinations over about a 2-month period in which the clones were grown.

TABLE 2

Specific Productivity of Clones derived from Clone 100d08

| Name | Average Specific Productivity |
|---|---|
| d08wn-01 | 9.16 |
| d08wn-03 | 8.60 |
| d08wn-04 | 10.75 |
| d08wn-13 | 8.08 |

TABLE 2-continued

Specific Productivity of Clones derived from Clone 100d08

| Name | Average Specific Productivity |
|---|---|
| d08wn-16 | 12.23 |
| d08wn-18 | 10.56 |

TABLE 3

Specific Productivity of Clones derived from Clone 100d12

| Name | Average Specific Productivity |
|---|---|
| d12u-02 | 8.71 |
| d12u-03 | 7.44 |
| d12u-04 | 8.83 |
| d12u-07 | 9.46 |
| d12u-09 | 8.63 |
| d12u-11 | 9.92 |
| d12u-14 | 7.51 |

TABLE 4

Specific Productivity of Clones derived from Clone 100d16

| Name | Average Specific Productivity |
|---|---|
| d16wn-01 | 11.76 |
| d16wn-02 | 12.22 |
| d16wn-03 | 12.93 |
| d16wn-05 | 11.22 |
| d16wn-06 | 12.24 |
| d16wn-07 | 13.08 |
| d16wn-08 | 10.50 |
| d16wn-12 | 9.07 |
| d16wn-13 | 9.90 |
| d16wn-19 | 11.94 |
| d16wn-20 | 10.15 |

TABLE 5

Specific Productivity of Clones derived from Clone 100d13

| Name | Average Specific Productivity |
|---|---|
| d13n-01 | 8.81 |
| d13n-14 | 7.51 |
| d13n-17 | 8.31 |
| d13n-18 | 8.77 |
| d13n-19 | 8.69 |
| d13n-20 | 8.08 |
| d13n-21 | 7.71 |
| d13n-22 | 8.57 |
| d13n-23 | 7.81 |

TABLE 6

Specific Productivity of Clones derived from Clone 300d01

| Name | Average Specific Productivity |
|---|---|
| d01u-06 | 8.51 |
| d01u-07 | 8.17 |
| d01u-08 | 8.97 |

TABLE 7

Specific Productivity of Clones derived from Clone 30d17

| Name | Average Specific Productivity |
|---|---|
| d17w-02 | 6.10 |
| d17w-05 | 7.17 |
| d17w-06 | 7.57 |
| d17w-09 | 10.61 |
| d17w-10 | 7.10 |
| d17w-11 | 8.10 |
| d17w-14 | 7.80 |
| d17w-17 | 10.67 |

TABLE 8

Specific Productivity of Clones derived from Clone 30d18

| Name | Average Specific Productivity |
|---|---|
| d18u-01 | 3.83 |
| d18u-02 | 2.60 |
| d18u-03 | 4.07 |
| d18u-13 | 8.29 |
| d18u-19 | 5.76 |

TABLE 9

Specific Productivity of Clones derived from Clone 30d22

| Name | Average Specific Productivity |
|---|---|
| d22u-01 | 6.35 |
| d22u-02 | 5.60 |
| d22u-03 | 6.12 |
| d22u-04 | 5.29 |
| d22u-05 | 4.85 |
| d22u-06 | 5.74 |
| d22u-07 | 6.08 |
| d22u-08 | 5.25 |
| d22u-09 | 5.18 |
| d22u-10 | 7.36 |
| d22u-11 | 2.94 |
| d22u-12 | 5.11 |
| d22u-13 | 7.77 |
| d22u-14 | 11.70 |

Thus, from the results set forth in Tables 1–9 it is apparent that: Clones 100d08 produced about 7 $\mu$g/10$^6$ cells/24 hours at the time the MTX treatment was started. Selection with 5 $\mu$M MTX enabled the isolation of clones producing an average of 10 or 12 $\mu$g/10$^6$ cells/24 hours. This represents an increase of about 50–70%. Clones 100d16 produced about 4.6 $\mu$g/10$^6$ cells/24 hours at the time the MTX treatment was started. Selection with 5 $\mu$M MTX enabled the isolation of clones producing averages of about 12 or 13 $\mu$g/10$^6$ cells/24 hours. This represents an increase of about 260–280%. Clones 100d13 produced relatively low levels (1.5 $\mu$g/10$^6$ cells/24 hours) of TBP-I at the time the MTX treatment was started. Selection with $\mu$M MTX enabled the isolation of clones producing averages of 8 $\mu$g/10$^6$ cells/24 hours. This represents an increase of about 500%. Although the starting productivity was low, this increase in productivity is very impressive, especially considering that it has been achieved with only 2 $\mu$M MTX. Clones 300d01 and 30d17 increased their productivity by about 100% upon MTX treatment. Most of the clones isolated by treatment of clone 30d18 with 4 $\mu$M MTX showed no enhancement in productivity. A few showed a two-fold increase.

In view of the above, it may therefore be concluded that:
1) It is possible to inhibit the mRNA expressed from the DHFR gene by transfection of an anti-sense DHFR sequence and subsequent hybridization with an anti-sense DHFR RNA sequence;
2) Following hybridization and inhibition of the DHFR gene, it is possible to carry out gene amplification by treating cells with MTX. The MTX concentration required for efficient amplification is lower than that used for the isolating and amplifying the initial DHFR$^+$ clone; and
3) By using the anti-sense DHFR approach, TBP-I productivity was improved by two-to five-fold in several clones.

(C) Specific Productivity of TBP-I in the Selected MTX-sensitive Clones Derived from Parental CHO Clone SK-108-1-22-12

Following the procedures set forth in section (B) above for the SBV14-24-derived clones, SK-108-1-22-12-derived clones were also assayed for TBP-I specific productivity.

The parental clone was shown to have an average specific productivity of 3.01±1.28 $\mu$g TBP-I/10$^6$ cells/24 hours.

The neomycin resistant, anti-sense DHFR-carrying clones derived from the parental clone were shown to have TBP-I specific productivities of average values ranging from 1.25 to 7.70 $\mu$g/10$^6$ cells/24 hours, most however having values comparable to that of the parental clone (results not shown). Nevertheless, these neomycin-resistant SK-108-1-22-12-derived clones, some of which are capable of increased TBP-I specific productivity, illustrate that transfection with the anti-sense DHFR carrying plasmid was likewise successful and that the anti-sense DHFR sequence was expressed in these clones.

Thus, from the results presented in Examples 1 and 2 above, it may be concluded that:
1) A second transfection can be performed with an anti-sense expression vector in clones that have already been prepared by a first transfection, to become desired protein (TBP-I) producing clones. In order to monitor and select clones successfully transfected by the second transfection, a second selectable genetic marker (eg. neomycin-resistance) besides the DHFR$^+$ used for the initial transfection is required in the plasmid/vector for the second transfection.
2) By introducing a normal gene (DHFR) and placing it in its reverse orientation under the transcriptional control of a promoter (eg. SV40 early promoter) which transcribes the gene according to its reversed orientation, it is possible to produce an anti-sense RNA complementary to the normally transcribed mRNA (the normal gene being present in the cells from the first transfection) and capable of binding to the normal mRNA thereby leading to an inhibition in the translation of the normal transcribed mRNA and hence a reduction in the level of the normal gene product (DHFR).

The level of translation inhibition of DHFR mRNA depends on the relative levels of expression of the two DHFR sequences, partial inhibition being achieved when the normal gene sequence is expressed at higher levels than the anti-sense sequence. In the examples described above, the TBP-I producing clones are established MTX-resistant clones, i.e., selected after extensive growth in the presence of MTX. This selection leads to an amplification of the integrated DHFR sequence as well as its surrounding sequences (eg. that encoding TBP-I) in these clones thus giving rise to relatively high DHFR expression levels as a result of MTX-induced amplification of DHFR gene copy number. Accordingly, following the second transfection, the anti-sense DHFR sequence newly integrated into the clones is in lower copy numbers relative to the normal DHFR sequence, and consequently, normal DHFR was usually observed to be only partially inhibited. Indeed, DHFR inhibition must be only partial in all surviving clones grown in the presence of MTX, otherwise, complete inhibition would lead to MTX-induced cell death. This partial inhibition of DHFR in the surviving selected clones therefore provides clones which have been rendered more responsive/sensitive to MTX and the DHFR-induced inhibition of MTX is consequently reduced in these clones.

3) Selected clones treated with MTX were rendered more sensitive to MTX by transfection with the anti-sense DHFR thereby permitting the selection and isolation of clones having significantly higher desired protein (TBP-I) production, namely, between 2–5 fold (200–500%) increases) increase in specific productivity.

EXAMPLE 3

Increasing Responsiveness to Gene Amplification for the Ornithine Decarboxylase (ODC) in Wild-type CHO Cells (ODC$^+$)

The purpose of this hypothetical Example is to illustrate how the amplification method of the present invention can be adapted to systems other than DHFR/MTX.

An ODC expression vector is to be constructed similar to the plasmid pdhOD1 as described in Chiang et al. *Mol. Cell. Biol.* 8:764–769 (1988) where the mouse ODC gene is flanked by SV40 early promoter and SV40 polyadenylation signals. The DHFR expression unit shown on pdhOD1 can be replaced with the gene encoding the protein of choice and a promoter for expressing such a gene. The type of promoter used for expressing the protein of choice is described above.

Wild-type CHO host cells for transfection that are ODC$^+$ can be maintained on Dulbecco modified Eagle medium containing 10% fetal calf serum. Alternatively, ODC-deficient (ODC$^-$) CHO cells such as C55.7 can be used as the host for transfection with the ODC expression vector. ODC$^-$ CHO cells are to be grown as described in Steglich et al., *Somatic Cell Mol. Genet.* 11(1):11–23 (1985).

CHO host cells transfected with the ODC expression vector is to be selected for resistance to serially increasing levels of difluoromethyl ornithine (DFMO), a suicide-substrate inhibitor of ODC, such as sequential selection for resistance to 160 $\mu$M, 600 $\mu$M, 1 mM, 3 mM, 9 mM and 15 mM DFMO. Following transfection, approximately $10^5$ cells are to be plated per 100 mm dish into medium containing DFMO, and the plates are to be refed with fresh medium every 5 days until a resistant population emerges. The level of expression of ODC and the protein of choice can be readily determined in DFMO-resistant CHO cells.

DFMO-resistant CHO cells showing high level expression of the protein of choice can be used as host cells to be transfected/transformed with an anti-sense expression plasmid vector constructed to carry an anti-sense ODC gene in a manner similar to that described in Example 1. Expression of anti-sense ODC RNA in DFMO-resistant CHO cells carrying amplified copies of both the ODC gene and the desired gene (encoding the protein of choice) will increase cell sensitivity to lower amounts of added DFMO, thereby increasing cell responsiveness to further amplification at lower levels of DFMO. As in the case of DHFR/MTX, ODC/DFMO will permit further amplification of the desired gene as well as a concomitant increase in the level of expression of the protein of choice.

What is claimed is:

1. A transformed mammalian cell, in cell culture, for expressing a protein of interest, said mammalian cell comprising:
   a directly amplifiable gene sequence, in expressible form, which when expressed renders said cell more resistant to a toxic agent, said sequence being exogenous to said cell;
   a gene of interest, in expressible form, which encodes a desired protein foreign to said cell; and
   an anti-sense gene sequence, in transcribable form, encoding an anti-sense RNA which selectively hybridizes in said cell to at least a portion of the mRNA transcribed from said directly amplifiable gene sequence so as to inhibit the translation of said mRNA, such that a higher level of amplification of said directly amplifiable gene and said gene of interest can be achieved, if the cell is exposed to a sufficient level of the toxic agent, than in the absence of said anti-sense RNA, wherein the directly amplifiable gene encodes a dihydrofolate reductase (DHFR) and the toxic agent is methotrexate (MTX).

2. The transformed cell of claim 1, wherein said mammalian cell is a CHO cell.

3. The transformed cell of claim 1, wherein said desired protein is selected from the group consisting of interleukins (ILs), interferons (IFNs), cell-bound receptors, and soluble receptors.

4. The transformed cell of claim 1, wherein said desired protein is soluble Type 1 tumor necrosis factor (TNF) binding protein I (TBP-I).

5. The cell of claim 1, wherein the DHFR gene is a mouse DHFR gene or cDNA.

6. An expression enhancing vector for regulating DHFR gene expression in a mammalian cell, comprising:
   a double-stranded sequence encoding a DHFR gene having a sense orientation and an anti-sense or reverse orientation;
   a first promoter sequence oriented so that said promoter sequence transcribes said DHFR sequence in the anti-sense orientation; and
   a second promoter sequence oriented so that said second promoter sequence transcribes said DHFR sequence in the sense orientation,
   said cell being DHFR⁻, MTX-resistant and capable of producing a desired protein, said expression enhancing vector, when transfected into and expressed in said cell, causes said cell to produce anti-sense DHFR RNA complementary to the sense DHFR mRNA produced in said cell, said anti-sense DHFR RNA selectively hybridizing to the sense DHFR mRNA, thereby increasing MTX sensitivity/responsiveness and increasing the production of said desired protein in said cell.

7. The vector of claim 6, wherein the DHFR gene is a mouse DHFR gene or cDNA.

8. A method for regulating the production level of a desired protein in a transformed mammalian cell, comprising the steps of:
   providing a transformed cell of claim 1 producing said desired protein, the level of said desired protein being at least partly regulated by the toxic product-amplified copy number of said gene of interest;
   expressing said anti-sense gene sequence and producing anti-sense RNA complementary to and specifically hybridizing with mRNA produced by transcription from said directly amplifiable gene sequence, thereby inhibiting the translation of said mRNA and leading to decreased levels of enzyme production; and
   adding additional toxic agent to further amplify said toxic agent-amplified copy number of said gene of interest thereby increasing the expression and production of said desired protein, in which the directly amplifiable gene encodes a DHFR and the toxic agent is methotrexate.

9. The method of claim 8, wherein said cell is a CHO cell.

10. The method of claim 8, wherein said desired protein is selected from the group consisting of interleukins (ILS), interferons (IPNs), cell-bound receptors and soluble receptors.

11. The method of claim 8, wherein said desired protein is soluble Type 1 TNF receptor (TBP-I).

12. The vector of claim 6, where the DHFR gene in its sense orientation encodes a mammalian DHFR protein.

13. The vector of claim 6, where said first and second promoter sequences are each independently selected from promoters native to mammalian genes or from genes of viruses which in fact mammalian cells.

* * * * *

SEQUENCE LISTING

<160> NUMBER OF SEQ ID NOS: 2

<210> SEQ ID NO 1
<211> LENGTH: 22
<212> TYPE: DNA
<213> ORGANISM: Artificial Sequence
<220> FEATURE:
<223> OTHER INFORMATION: Description of Artificial  Sequence: Part of
      adaptor used in construction of plasmid containing DHFR
      sequence in pSVE3

<400> SEQUENCE: 1
agctcagatc tcgtctagag ga                                              22

<210> SEQ ID NO 2
<211> LENGTH: 22
<212> TYPE: DNA
<213> ORGANISM: Artificial Sequence
<220> FEATURE:
<223> OTHER INFORMATION: Description of Artificial  Sequence: Part of
      adaptor used in construction of plasmid containing DHFR
      sequence in pSVE3

<400> SEQUENCE: 2
gtctagagca gatctccttc ga                                              22